United States Patent
Taylor

(10) Patent No.: US 9,739,757 B2
(45) Date of Patent: Aug. 22, 2017

(54) CONDITION CHANGE LABELS

(71) Applicant: TEMPTIME CORPORATION, Morris Plains, NJ (US)

(72) Inventor: Dene H. Taylor, New Hope, PA (US)

(73) Assignee: TEMPTIME CORPORATION, Morris Plains, NJ (US)

( * ) Notice: Subject to any disclaimer, the term of this patent is extended or adjusted under 35 U.S.C. 154(b) by 161 days.

(21) Appl. No.: 14/560,944

(22) Filed: Dec. 4, 2014

(65) Prior Publication Data

US 2015/0153315 A1  Jun. 4, 2015

Related U.S. Application Data

(60) Provisional application No. 61/911,871, filed on Dec. 4, 2013.

(51) Int. Cl.
*B32B 37/18* (2006.01)
*G01N 31/22* (2006.01)
*B32B 38/00* (2006.01)

(52) U.S. Cl.
CPC ......... *G01N 31/229* (2013.01); *B32B 37/185* (2013.01); *B32B 38/145* (2013.01); *B32B 2309/10* (2013.01); *B32B 2519/00* (2013.01); *G01N 31/222* (2013.01); *Y10T 156/10* (2015.01)

(58) Field of Classification Search
CPC .... Y10T 156/10; G01N 31/22; G01N 31/229; G01N 31/222; B32B 2519/00; B32B 2309/10; B32B 37/185; B32B 38/145; B32B 37/18; B32B 37/1284; B32B 37/12
USPC .......... 116/206–207, 216–220, 200
See application file for complete search history.

(56) References Cited

U.S. PATENT DOCUMENTS

| | | | | |
|---|---|---|---|---|
| 3,786,777 A | * | 1/1974 | Smith | G01K 11/06 116/206 |
| 3,822,189 A | * | 7/1974 | Tornmarck | G01K 3/04 374/E3.004 |
| 4,120,818 A | * | 10/1978 | Swindells | G01K 11/06 116/207 |
| 4,154,107 A | * | 5/1979 | Giezen | G01K 11/16 116/207 |
| 4,428,321 A | * | 1/1984 | Arens | G01K 3/04 116/207 |

(Continued)

FOREIGN PATENT DOCUMENTS

| | | | | |
|---|---|---|---|---|
| GB | 2457180 A | * | 8/2009 | B82Y 15/00 |
| WO | WO2007/148321 | | 12/2007 | |

OTHER PUBLICATIONS

PCT Search Report and Written Opinion dated Feb. 18, 2015 issued for International PCT Application No. PCT/US14/68614 filed Dec. 4, 2014.

(Continued)

*Primary Examiner* — R. A. Smith
*Assistant Examiner* — Tania Courson
(74) *Attorney, Agent, or Firm* — K&L Gates LLP

(57) ABSTRACT

Described herein are condition change labels, methods of forming them, and methods of using them. Generally, condition change labels include a first layer including a blister laminated to a first side of a bottom layer thereby creating a container; an indicator substance located in the container; and an adhesive disposed on at least a portion of a second side of the bottom layer, wherein the condition change label has a stiffness less than about 0.06 mN•m.

20 Claims, 13 Drawing Sheets

(56) References Cited

U.S. PATENT DOCUMENTS

| | | | |
|---|---|---|---|
| 4,448,548 A * | 5/1984 | Foley | G01N 31/226 252/408.1 |
| 4,587,158 A | 5/1986 | Ewing | |
| 4,643,122 A * | 2/1987 | Seybold | G01N 31/22 116/206 |
| 4,724,029 A | 2/1988 | Kontz | |
| RE32,929 E | 5/1989 | Ewing | |
| 5,151,309 A | 9/1992 | Dollinger | |
| 5,380,572 A | 1/1995 | Kotani et al. | |
| 5,435,963 A | 7/1995 | Rackovan et al. | |
| 5,982,284 A | 11/1999 | Baldwin | |
| 6,270,882 B1 | 8/2001 | Eggers | |
| 6,461,706 B1 | 10/2002 | Freedman et al. | |
| 6,534,006 B2 * | 3/2003 | Hehenberger | G01N 31/226 116/206 |
| 6,957,623 B2 | 10/2005 | Guisinger et al. | |
| 7,150,406 B2 | 12/2006 | Droz | |
| 7,158,031 B2 | 1/2007 | Tuttle | |
| 7,343,872 B2 * | 3/2008 | Taylor | G01K 1/02 116/216 |
| 7,399,509 B2 | 7/2008 | Virtanen | |
| 7,571,695 B2 | 8/2009 | Taylor et al. | |
| 7,891,310 B2 * | 2/2011 | Taylor | G01K 3/005 116/216 |
| 8,061,294 B2 * | 11/2011 | Suda | G01K 11/06 116/216 |
| 8,122,844 B2 | 2/2012 | Smith et al. | |
| 8,128,872 B2 | 3/2012 | Lentz et al. | |
| 8,430,053 B2 * | 4/2013 | Taylor | G01K 11/06 116/206 |
| 8,800,472 B2 * | 8/2014 | Park | G01K 3/04 116/219 |
| 2003/0214997 A1 | 11/2003 | Diekmann et al. | |
| 2010/0020846 A1 * | 1/2010 | Kagan | B82Y 15/00 374/141 |
| 2010/0024714 A1 | 2/2010 | Taylor et al. | |
| 2012/0079981 A1 | 4/2012 | Huffman et al. | |
| 2014/0048010 A1 | 2/2014 | Smith et al. | |
| 2015/0000588 A1 | 1/2015 | Newport et al. | |

OTHER PUBLICATIONS

Tappi Test Method T 489 om-04: Bending resistance (stiffness) of paper and paperboard (Taber-type tester in basic configuration), Tappi, Atlanta 2004.

ASTM Method D882, "Test methods for the tensile properties of thin plastic sheeting" American Society for Testing and Materials.

Barry A. Morris, John D. Vansant; The Influence of Sealant Modulus on the Bending Stiffness of Multilayer Films, DuPont. Originally presented in the 1997 TAPPI Polymers, Lamin.

J. Lange, C. Pelletier & Y. Wyser, Modeling and measuring the bending stiffness of flexible packaging materials. Paper, Film, & Foil Converter, Mar. 2002.

* cited by examiner

Prior Art

CONDITION CHANGE LABELS

CROSS REFERENCE TO RELATED APPLICATIONS

This application claims the benefit of U.S. provisional patent application No. 61/911,871, filed Dec. 4, 2013, the entire disclosure of which is incorporated herein by reference.

FIELD

Described herein are condition change labels for product housings.

SUMMARY

Described herein are condition change labels that can be applied to individual items such as product housings. Product housings can include bottles, vials, syringes, sterile bags and the like. In some example embodiments, product housings can be medical or biological related housings. The condition change labels can be sufficiently flexible to wrap a curved surface without flagging, can be sufficiently rigid to detach from a liner, can contain an indicator for the intended life of the housed substance, do not interact with housed substance or interfere with housed substance's functionality, can be accurate, can be reliable, can have a long shelf life, can function under a wide range of conditions, can be inexpensive, can be manufactured in large volumes at high speed, and can be usable with high speed labeling machinery.

Condition change labels can include: a first or top layer including a blister laminated to a first side of a bottom or second layer thereby creating a container; an indicator substance located in the container; and an adhesive disposed on at least a portion of a second side of the bottom layer. In one embodiment, the condition change labels have a stiffness less than about 0.6 mN·m.

Condition change labels described herein can have characteristics that permit them to be applied by a high speed label applicator, and which may be desirable in the supply of indicators for such devices. The condition change labels can also have upper limits of stiffness to provide flexibility, and lower levels of stiffness to provide rigidity. In one embodiment, the stiffness of a condition change label can be between about 0.001 mN·m and about 0.06 mN·m. A condition change indicator with a stiffness in this range can be stiff enough for application to a curved surface yet flexible enough to avoid flagging after application.

Condition change labels described herein can be used as chemical indicators for small items, such as vials, which are sensitive to decreasing as well as increasing temperature, and which may have multiple color changes with temperature including both reversible and irreversible changes; samples of colored paints for liquid color matching; samples of colored fluids on the outside of opaque containers such as cans and aerosols; colored cosmetic fluids; marketing samples attached to the packages of well-known brands, two part single use adhesive mixtures where there is a very small volume of an activator which is conveniently provided as a label-like item on the outside of a small container, tube or vial of the primary component; and the like.

BRIEF DESCRIPTION OF THE DRAWINGS

FIG. 13A is a top view of a sample for measurement. FIG. 13B is a side cross-section of the sample mounted in the measurement apparatus. FIG. 13C is a front view of the sample mounted in the measurement apparatus.

FIG. 14A is a top view of the activatable condition change label. FIG. 14B is a cross-section on the line M-M of FIG. 1A. FIG. 14C is a cross-section on the line N-N of FIG. 14A. FIG. 14D is a cross-section on the line P-P of FIG. 14A.

DETAILED DESCRIPTION

Figure 1A:
FIGS. 1A-D illustrate different stress responses.
Figure 1B:
Figure 1C:
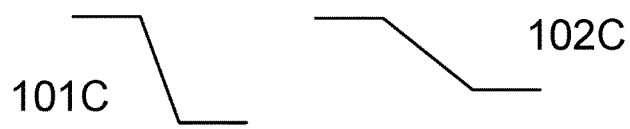
Figure 1D:

Described herein are condition change labels having a stiffness between about 0.001 mN·m and about 0.06 mN·m. In some embodiments, this stiffness range avoids flagging when applying the labels to cylindrical, conical, or substantially cylindrical or conical product housings such as vials or syringes. For example, in some embodiments, this stiffness range can allow condition change indicators to wrap cylinders as small as 10 mm in diameter and syringes of 6 mm in diameter. The labels can also be used on flat surfaces. Further, these condition change indicators can be targeted for use in high speed label applicators.

Stiffness as used herein is a defined and measurable material property. A common method for measurement of film and paper stiffness is TAPPI Method 849 using the Taber Stiffness Tester, which uses the units milliNewton·meter or mN·m. Stiffness may also be calculated from the modulus of elasticity which is measured by ASTM Method D822. The stiffness can be determined by selecting substrates so that the stiffness of the combined or laminated construction is within the range of between about 0.001 mN·m and about 0.06 mN·m.

Product housings can have different overall shapes and/or different particular label area shapes depending on the size of the product housing. Label areas can be portions of housings where a label is to be applied and although the remainder of the housing may have a different shape(s), the label area may have a differing shape such as one defined herein. Shapes of product housings and label areas can include flat, cylindrical, conical, or substantially cylindrical or conical. Product housings can have any size on which a label as described herein can be placed.

Condition change labels can include at least one volume, container, or blister for housing an indicator substance. An indicator substance as described herein can be a solid, liquid, gel, semi-solid, colloid, a mesh, or the like, or a combination thereof that can or is configured to change state, color, opacity, transparency, or a combination thereof upon introduction to a predetermined condition. For example, a clear colloid may become opaque or white when subjected to a predetermined condition. In some embodiments, the indicator substance goes from clear to opaque or darkly colored, or from opaque or darkly colored to clear, when the indicator is subjected to the predetermined condition. In some embodiments, the indicator substance is aqueous.

A predetermined condition can be a desired or undesired condition for which indication that such a condition has been met can be determined. For example, a predetermined condition may be freezing, boiling, a particular temperature or range of temperatures, exposure to light, exposure to a particular wavelength of light such as UV light, exposure to liquid such as humidity, exposure to excess pressure, subject to contamination such as bacteria, or the like, or a combination thereof. In one embodiment, the predetermined condition is freezing.

In one embodiment, a predetermined condition can be humidity above a particular percentage such as 65% relative humidity.

In another embodiment, a predetermined condition can be sunlight. For example, a condition change label that detects subjection to sunlight can be useful if the product requires no exposure to sunlight.

In one embodiment, a predetermined condition can be a freezing temperature. In such an embodiment, the indicator substance can be an essentially transparent freeze-sensitive colloid, which can appear to have a similar color to the bottom layer of a container. Upon freezing, the colloid becomes opaque and obscures the bottom of the container, and so the substance appears white.

If color change of an indicator substance is required, the color of the container's top layer can be important. For example, colors that might skew the visual color of the indicator substance may be avoided. Likewise, for indicator substances that transition from clear to opaque white, a white indicator container may be avoided to prevent confusion of state. Further, still, a deep red or pink container may not be suitable colors if the indicator was a gold colloid.

In other embodiments, should an indicator substance contain a freeze sensitive liquid that changes from one color to a different color on freezing or exposure to freezing conditions, then that color change can be reflected in the appearance of the indicator. That is, it can be readily obvious that the indicator, and therefore the contents of the product, have been exposed to potentially damaging conditions and appropriate action should be taken.

Dimensions of an indicator substance needed can require containers of different sizes (and volumes). The color change in an indicator substance can be obvious at arms length, in both strong and weak light. However, in some embodiments, the change is not obvious and can require special equipment to read the state of the indicator. In the absence of an adjacent reference or contrast, a difference of 0.4 optical density units can be reliable, when either the starting or ending point is white or close to white.

In other embodiments, a change may be more or less intense. The color in this type of indicator substance can be produced in a liquid, so Beer's law can be applied to relate the color to the thickness of the liquid, or depth of the indicator as defined here. When the color change intensity is increased, the depth can be proportionally reduced. And if the change is weaker, the indicator may be deeper. As an example, the colloid used in the FREEZE CHECK® indicator can allow the background to be seen in the un-exposed indicator, yet obscures it thoroughly when the indicator has been exposed to freezing conditions.

In some embodiments, good visibility of the indicator in ordinary lighting at arms length can be achieved with a square or circle container with a diameter of about 4 mm, or a similar width if rectangular, with suitable immediate contrast. Larger or smaller indicators may be appropriate in different circumstances or with different changes in contrast between the fresh and exposed states.

In one embodiment, a volume or container for housing an indicator substance does not interfere with labeling performance of a container. The volume or container for housing an indicator substance can be less than about 0.5 mm, less than about 0.4 mm, less than about 0.3 mm, less than about 0.2 mm, less than about 0.1 mm, less than about 0.09 mm, less than about 0.08 mm, less than about 0.07 mm, less than about 0.06 mm, less than about 0.05 mm, at least about 0.01 mm, at least about 0.05 mm, about 0.5 mm, about 0.4 mm, about 0.3 mm, about 0.2 mm, about 0.1 mm, about 0.09 mm, about 0.08 mm, about 0.07 mm, about 0.06 mm, about 0.05 mm, about 0.04 mm, about 0.03 mm, about 0.02 mm, about 0.01 mm, between about 0.5 mm and about 0.01 mm, between about 0.2 mm and about 0.05 mm, or between about 0.2 mm and about 0.01 mm thick.

Small containers can include a volume less than about 5 µL, less than about 4 µL, less than about 3 µL, less than about 2 µL, or less than about 1 µL. Larger containers can have volumes of more than about 5 µL, more than about 25 µL, more than about 50 µL, more than about 500 µL, or more than about 5 mL.

The volume can be sealed so that no contents of the indicator substance are lost as a result of leakage. The volume can be shaped to minimize structural stiffness. For example, shapes can include circular, square, triangular, or any other rectilinear or curved shapes. The size can be less than about 10 mm, less than about 9 mm, less than about 8 mm, less than about 7 mm, less than about 6 mm, less than about 5 mm, at least about 1 mm, at least about 2 mm, about 10 mm, about 8 mm, about 7 mm, about 6 mm, about 5 mm, between about 7 mm and about 5 mm, between about 10 mm and about 5 mm, between about 8 mm and about 5 mm in diameter or rectilinear measurement (for example, a longest side).

In one embodiment, the volume has a transparent or substantially transparent top or top layer. This top layer can also be referred to as a first layer. Substantially transparent can include any degree of transparency that allows detection of a change in the indicator substance resulting from a condition change, such as greater than about 80% transparent, greater than about 90% transparent, greater than about 95% transparent, greater than about 96% transparent, greater than about 97% transparent, greater than about 98% transparent, or greater than about 99% transparent.

Further, the top can be embossed or blistered to a depth of less than about 0.5 mm, less than about 0.4 mm, less than about 0.3 mm, less than about 0.2 mm, less than about 0.1 mm, at least about 0.01 mm, at least about 0.05 mm, at least about 0.1 mm, about 0.5 mm, about 0.4 mm, about 0.3 mm, about 0.2 mm, about 0.1 mm, between about 0.5 mm and about 0.1 mm, between about 0.4 mm and about 0.1 mm, or between about 0.3 mm and about 0.1 mm.

The top layer can be formed of a material or film that forms a barrier to the indicator substance such that it substantially prevents the substance of its vapor from escaping or leaching through over time. The material can include a polymer such as poly(L-lactic acid), polycaprolactone, poly(lactide-co-glycolide), poly(ethylene-vinyl acetate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g., PEO/PLA), polyurethanes, silicones, polyesters, polyolefins, polyisobutylene and ethylene-alpha-olefin copolymers, acrylic polymers and copolymers, ethylene-co-vinylacetate, polybutylmethacrylate, vinyl halide polymers and copolymers (e.g., polyvinyl chloride), polyvinyl ethers (e.g., polyvinyl methyl ether), polyvinylidene halides (e.g., polyvinylidene fluoride and polyvinylidene chloride), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyimides, polyethers, polyurethanes, polypropylene, cellophane, carboxymethyl cellulose, and combinations thereof. In one embodiment, the top layer can be formed of polypropylene. If the indicator substance is water based, polypropylene can be an acceptable water barrier thereby preventing escape or diffuse through over time. Further, the material used to form the top layer can be chosen such that it does not react with the indicator substance. In an embodiment, oil when used as substance indicator can be contained between two layers of about 25 µm thick polyester film.

In some embodiments, the top layer can be formed of a material that can be printed on or can be printable.

The top layer can have a thickness that includes one or more of the characteristics described above. The thickness can be less than about 60 µm, less than about 50 µm, less than about 40 µm, less than about 30 µm, less than about 20 µm, at least about 0.5 µm, at least about 1 µm, at least about 5 µm, about 60 µm, about 50 µm, about 40 µm, about 30 µm, about 20 µm, about 10 µm, about 5 µm, about 1 µm, between about 60 µm and about 1 µm, between about 50 µm and about 10 µm, between about 40 µm and about 20 µm, between about 40 µm and about 10 µm, or between about 40 µm and about 1 µm.

Containers can also include a bottom or second layer, lid, or lidding stock. In some embodiments, the bottom layer of the container is opaque. However, in other embodiments, such as when the container is opaque, the bottom layer can be transparent or partially transparent.

The bottom layer can be formed of a material, foil or film that forms a barrier to the indicator substance such that it substantially prevents the substance of its vapor from escaping or leaching through over time. The bottom layer can be a foil, a polymer, or a combination thereof. Foils can be formed of metals or metal alloys, or either coated with a polymer such as, but not limited to stainless steel, aluminum, brass, iron, cobalt, steel, tin, etc. Polymers can be poly(L-lactic acid), polycaprolactone, poly(lactide-co-glycolide), poly(ethylene-vinyl acetate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g., PEO/PLA), polyurethanes, silicones, polyesters, polyolefins, polyisobutylene and ethylene-alpha-olefin copolymers, acrylic polymers and copolymers, ethylene-co-vinylacetate, polybutylmethacrylate, vinyl halide polymers and copolymers (e.g., polyvinyl chloride), polyvinyl ethers (e.g., polyvinyl methyl ether), polyvinylidene halides (e.g., polyvinylidene fluoride and polyvinylidene chloride), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyimides, polyethers, polyurethanes, polypropylene, cellophane, carboxymethyl cellulose, and combinations thereof. In one embodiment, the bottom layer can be formed of polypropylene. If the indicator substance is water based, polypropylene can be an acceptable water barrier thereby preventing escape or diffuse through over time. Further, the polymer used to form the bottom layer can be chosen such that it does not react with the indicator substance.

In some embodiments, the bottom layer can be formed of a material that can be printed on or can be printable. Specifically, a non-adhesive side of the bottom layer can be printable. In some embodiments, the bottom layer can include a heat seal coating.

The bottom layer can have a thickness that includes one or more of the characteristics described above. The thickness can be less than about 60 µm, less than about 50 µm, less than about 40 µm, less than about 30 µm, less than about 20 µm, at least about 0.5 µm, at least about 1 µm, at least about 5 µm, about 60 µm, about 50 µm, about 40 µm, about 30 µm, about 20 µm, about 10 µm, about 5 µm, about 1 µm, between about 60 µm and about 1 µm, between about 50 µm and about 10 µm, between about 40 µm and about 20 µm, between about 40 µm and about 10 µm, or between about 40 µm and about 1 µm. In one embodiment, the thickness of the bottom layer is less than about 25 µm.

The parts described herein (e.g., top layer, bottom layer, etc.) can be incorporated into the design of the mold used in the injection molding process to produce items of the commercial designs. However, because of the small size of the parts involved, it may be convenient to produce them in strings, sheets or webs, joined by threads of the polymer so that they can be readily oriented for the step where they are combined with the flip top component.

When combined, the top and bottom layers can form a structure that is less than about 65 μm, less than about 60 μm, less than about 55 μm, less than about 50 μm, less than about 45 μm, at least about 1 μm, at least about 2 μm, at least about 10 μm, about 65 μm, about 60 μm, about 55 μm, about 50 μm, about 45 μm, about 40 μm, about 35 μm, about 30 μm, about 25 μm, about 20 μm, about 10 μm, about 5 μm, about 2 μm, between about 65 μm and about 40 μm, between about 65 μm and about 50 μm, between about 65 μm and about 30 μm, between about 50 μm and about 40 μm, or between about 50 μm and about 30 μm. In one embodiment, the thickness of the combined layers is less than about 65 μm.

The top layer and the bottom layer can be combined to form a laminate material. That laminate material can have a stiffness comparable to 65 μm oriented polypropylene. Further, as with the individual layers, the laminate can be printed on or can be printable.

Condition change labels can optionally include an adhesive layer disposed on the back surface of the bottom layer. The adhesive layer can include a pressure sensitive adhesive, a hot melt adhesive, or the like, or a combination thereof. The adhesive used can have sufficient adhesive strength to hold a condition change label onto a cylindrical or otherwise curved surface without substantial flagging. The properties of a particular adhesive can be dependent on the surface material for attachment.

Condition change labels can also optionally include a liner attached to the adhesive layer before attachment to a surface. In some embodiments, the liner is a release liner. The liner can be sufficiently strong as to be used in a high speed automated label applicator. Further, release characteristics of the liner may be matched to the adhesive so there is appropriate release of the label from the liner in an automated label applicator operating at high speed. In some embodiments, the liner can be a continuous liner.

The liner can be formed of a material selected from paper, polymer or co-polymer, or paper coated with polymer such as polyethylene. Polymers may be polyethylene, polypropylene or poly terephthalate. Liners may be coated with a release layer such as silicone.

Condition change labels when fully constructed can have a size of less than about 10 mm, less than about 9 mm, less than about 8 mm, less than about 7 mm, less than about 6 mm, less than about 5 mm, at least about 2 mm, at least about 5 mm, about 10 mm, about 8 mm, about 7 mm, about 6 mm, about 5 mm, between about 7 mm and about 5 mm, between about 10 mm and about 5 mm, between about 8 mm and about 5 mm in diameter or rectilinear measurement (for example, a longest side).

Most currently available indicators are not suited for unit application to vials and syringes because they do not exhibit characteristics of a vial label. Rather, they can be too stiff to wrap a vial or syringe, can be too bulky to be supplied in roll form, and/or can be too stiff and bulky for high speed application. Some currently available indicators can be have a stiffness too high to be usable as described herein. For example, high stiffness can result from a thick multi-layer film construction with high tensile PET skins, and also from a bulky dispersion container such as a blister. These properties do not allow for currently available indicators to be used as vial labels. In some embodiments, in order to be useful as a label according to the present description, a condition change label can be comparably flexible and the dispersion container is thin and also flexible. Some rigidity may be necessary during application, for example, if not rigid enough, the condition change label may not release from a liner.

Flagging is a result of the stress used to deform an elastic material overcoming the localized adhesion of the adhesive to either the indicator or the curved surface. Many labels can be prone to creep, which concentrates the stress and initiates flagging. Flagging does not occur if the adhesive does not creep, and/or the adhesive strength greatly exceeds the stress. Although strong adhesives are available, they are not effective with commercially available highly stiff indicators.

Condition change labels, for example miniaturized labels, can be readily made by laminating together two liquid-impervious substrates. In one embodiment, the two liquid impervious substrates are films. In some embodiments, the films can be made of the same material. In other embodiments, the films can be made of different materials.

Condition change labels can include a substance container to house an indicator substance such as a liquid container if the indicator substance is a liquid. The substance container may be formed in one of the substrates, and then filled immediately before the two substrates are joined and sealed. The indicator substance might also be provided as a pad of saturated porous matrix instead of as a liquid. Such a pad can be placed on one or other substrate and then contained by sealing around it.

A label's total thickness is greatest at the container portion which is thicker than the area around the container where the label can consist of laminate alone. As liquids are incompressible this can potentially increase the stiffness so that the localized stiffness of the container portion falls outside the target range. However, as described herein, this overly stiff container can be overcome by allowing the container to deform.

One factor that may contribute to the extension of the perimeter of a container is its height. There is a direct relationship between the two dimensions. Therefore, it may be desirable to minimize the thickness of the container, for example by appropriate selection of intensely colored formulations for the visual indication at low volumes.

Additionally the surface forming the container's perimeter can be spring-like. A coil spring, for example, is a structure that can extend under a fixed force by dimensions that can be orders of magnitude greater than the extension of the equivalent length of straight wire or rod under the same force. The difference is that the spring uses bending, not stretching, and a small bend can translate into a substantial extension. By using bending instead of stretching the perimeter can be increased as the container is deformed with little force, even when formed from high tensile polymers. The simplest springs use a V or Z structure (FIGS. 1A and 1C), which extend easily under stress. Structure 101A illustrates a V-shaped structure with no applied force, while structure 102A illustrates the same V-shaped structure deformed by a laterally applied force. Similarly, structure 101C illustrates a Z-shaped structure with no applied force, while structure 102C illustrates the same Z-shaped structure deformed by a laterally applied force. Based on the V and Z structure, structures based on curves can be preferred and are illustrated in FIGS. 1 B and D. Structure 101B illustrates a curve based on a V-shaped structure with no applied force, while structure 102B illustrates the same curve deformed by a laterally applied force. Similarly, structure 101D illustrates a curve based on a Z-shaped structure with no applied force, while structure 102D illustrates the same curve deformed by a laterally applied force.

Figure 2A:
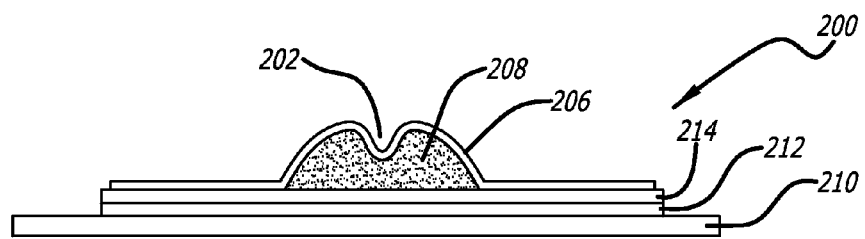
FIG. 2A is a side cross-sectional view of an example condition change label.
Figure 2B:
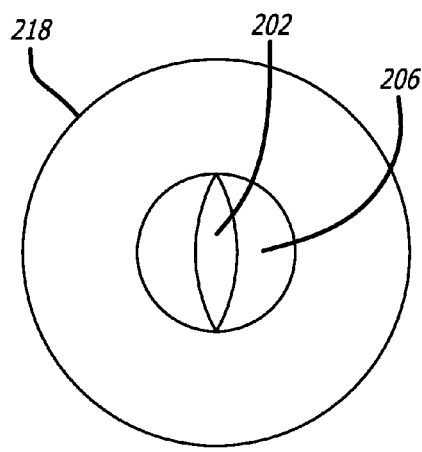
FIG. 2B is a top view of the condition change label.
Figure 2C:
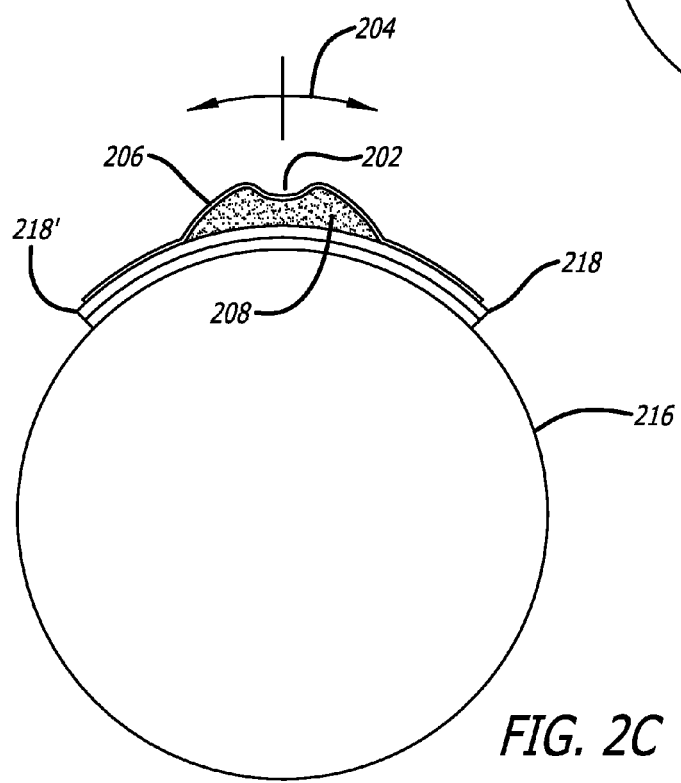
FIG. 2C is an illustration of the condition change label applied to a product housing.

Further, an indentation in the container's surface can also be used. For example, as illustrated in FIGS. 2A-C, an indentation 202 such as a groove or a crease perpendicular to a direction of stress 204 can be used. Indentation 202 can reside in blister 206 which houses indicator substance 208. Before use, label 200 is attached to a liner 210 with an adhesive 212 applied to bottom layer 214. As stress 204 is applied perpendicular to indentation 202, for example by placing the label 200 on a product housing 216, indentation 202 expands thereby alleviating stress at the periphery 218.

The size of the groove or indentation can be determined by the extension that is required in the perimeter of the cross-section to let the container wrap the smallest cylinder or vial that the indicator is designed to be attached to. In one embodiment, deformations in the container are made in forming the film in the top layer. It has also been found experimentally that when liquid filled indicators are attached to small diameter vials by hand using strong adhesives, the forming film stretched. Some indicators on the vials were heated to 65° C. for an hour, cooled to room temperature, and then detached from the vials. When laid flat they had grooves or creases in the top film as described above. This can then be a manner in which to determine the appropriate size and shape of the spring-like structure or to form a template.

Figure 3A:
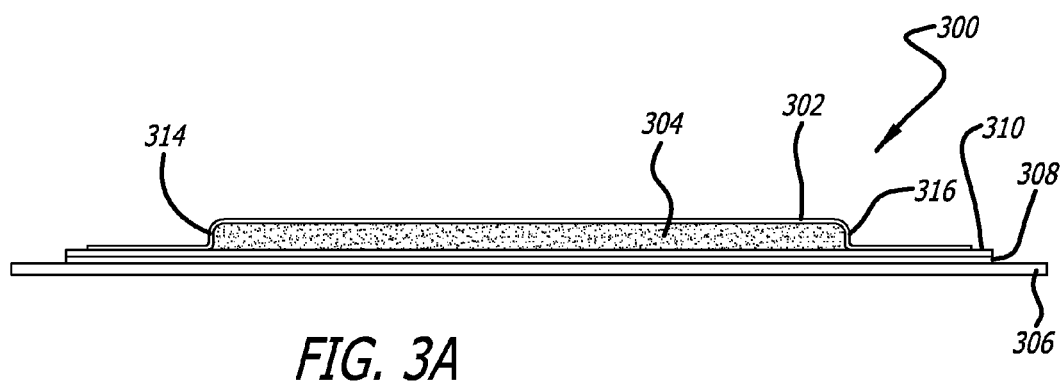
FIG. 3A is a side cross-sectional view of another example condition change label.
Figure 3B:
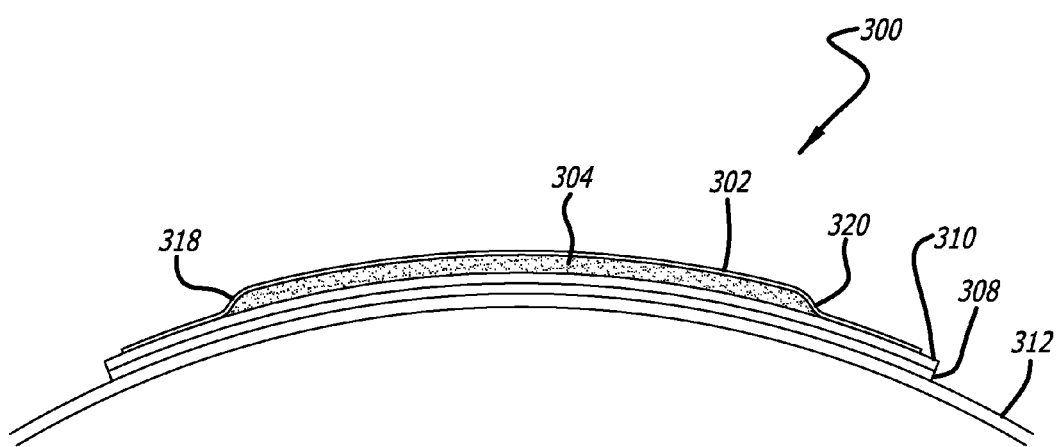
FIG. 3B is a cross-sectional view of the condition change label of FIG. 3A applied to a product housing.

In other embodiments, it may be desirable to provide extensibility to shallow and/or wide containers. A square or rectangular container can often be used because it provides greater structural stability to single lane rolls of items for the label applicator, than does an elliptical or circular form. When such a structure is shallow the extensibility can be obtained from the leading and trailing sides. On forming these have an angle relative to the plane of the bottom film/foil approaching a right angle. On wrapping about a cylinder, the angle increases by an amount related to the size of the arc formed by the container on the cylinder surface. FIGS. 3A-B illustrates this angle increase.

In FIGS. 3A-B, label 300 includes blister 302 which houses indicator substance 304. Before use, label 300 is attached to a liner 306 with an adhesive 308 applied to bottom layer 310. As stress is applied to label 300, for example by placing the label 300 on a cylindrical product housing 312, first edge 314 and second edge 316 stretch in the z-spring direction thereby creating first tensioned edge 318 and second tensioned edge 320. Although blister 302 is shallower in FIG. 3B than it was before it was applied in FIG. 3A, it retains a consistent depth.

Figure 4A:
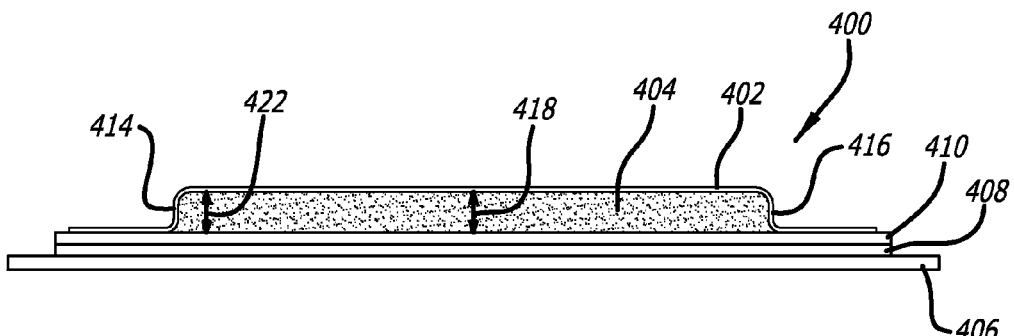
FIG. 4A is a side cross-sectional view of another example condition change label.
Figure 4B:
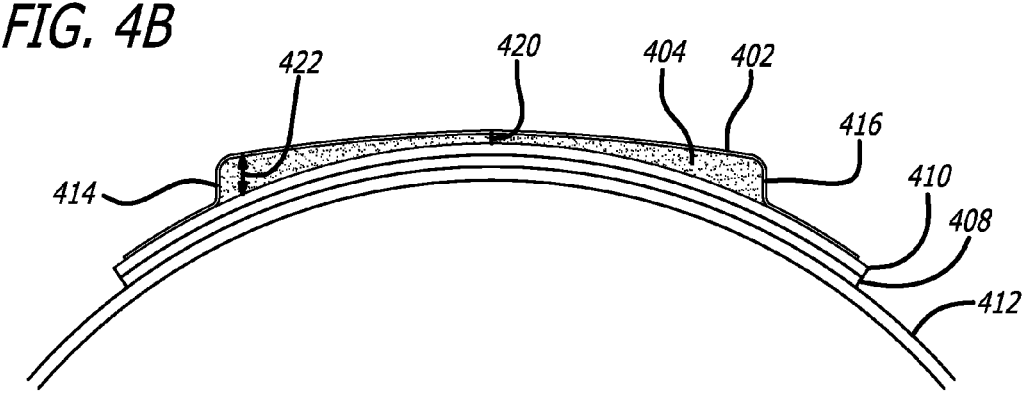
FIG. 4B is a cross-sectional view of the condition change label of FIG. 4A applied to a product housing.

In some embodiments, it may be desirable to vary depth within a broad container. For example, broad and/or shallow containers, such as those described above, may be prone to a variation(s) in depth as illustrated in FIGS. 4A-B. In FIGS. 4A-B, label 400 includes blister 402 which houses indicator substance 404. Before use, label 400 is attached to a liner 406 with an adhesive 408 applied to bottom layer 410. As stress is applied to label 400, for example by placing the label 400 on a cylindrical product housing 412, first edge 414 and second edge 416 do not stretch in the z-spring direction. As such, distance 418 becomes reduced distance 420 once applied to product housing 412, while edge distance 422 remains the same. In such an embodiment, if filled with a visual indicator substance, the intensity of the indication may vary substantially from the center to the periphery.

Figure 5A:
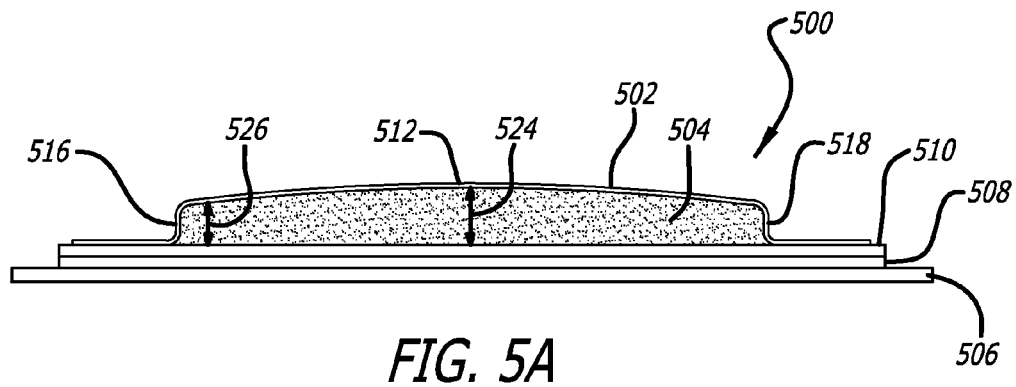
FIG. 5A is a side cross-sectional view of another example condition change label having a lenticular blister.
Figure 5B:
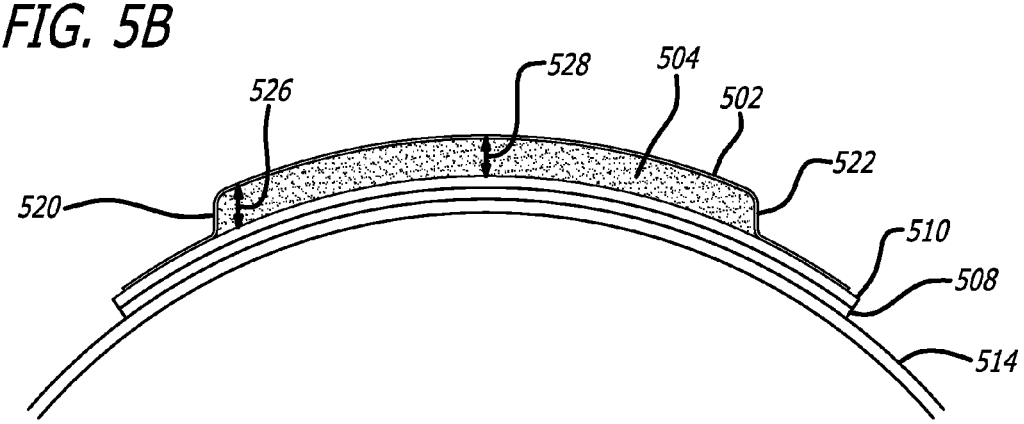
FIG. 5B is a cross-sectional view of the condition change label of FIG. 5A applied to a product housing.

In some embodiments, in order to overcome this variation in depth, a lenticular blister can be used. Shallowness of a container when wrapped can be prevented by forming the thin flat-bottomed container with a slight lenticular shape as illustrated in FIGS. 5A-B. In FIGS. 5A-B, label 500 includes blister 502 which houses indicator substance 504. Before use, label 500 is attached to a liner 506 with an adhesive 508 applied to bottom layer 510. Here, blister 502 has a lenticular shape 512 toward its center. As stress is applied to label 500, for example by placing the label 500 on a cylindrical product housing 514, first edge 516 and second edge 518 do stretch in the z-spring direction thereby creating first tensioned edge 520 and second tensioned edge 522. Likewise, center distance 524 although slightly larger than edge distance 526 because of the lenticular shape 512 of label becomes reduced, equal distance 528 once applied to product housing 514, while edge distance 526 remains the same.

Providing a lenticular shape can ensure that the perimeter of the center cross-section will be slightly longer than at the edges, and will experience slightly less stress on wrapping, which in turn avoids the top film from being drawn down to the bottom film.

In still other embodiments, maintaining consistent depth of broad container can be achieved using a multi-chamber structure. A multi-chamber structure may be used if a lenticular shaped container impedes manufacturing or performance. A multi-chamber structure can include a series of attached compartments with the boundaries or walls of the adjacent compartments made during blister formation. In one embodiment, the attached compartments can be narrow and/or rectangular.

Figure 6A:
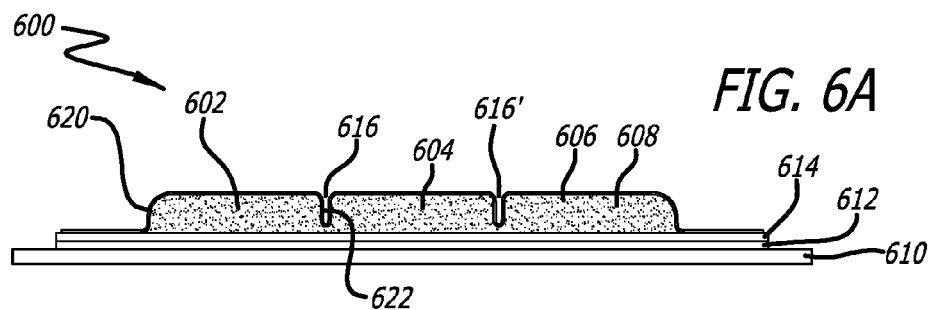
FIG. 6A is a side cross-sectional view of an example condition change multi-chamber label.
Figure 6B:
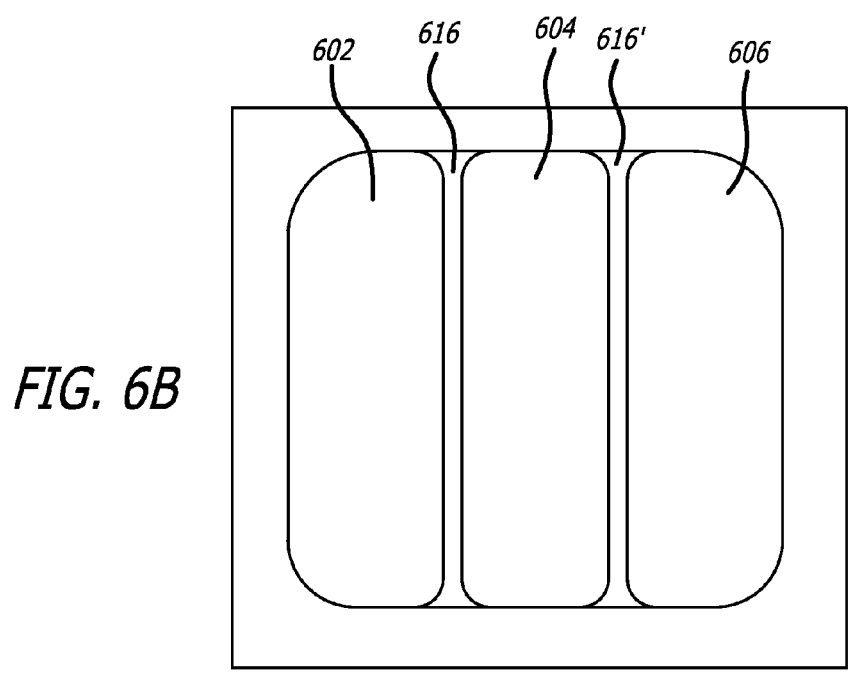
FIG. 6B is a top view of the condition change multi-chamber label.
Figure 6C:
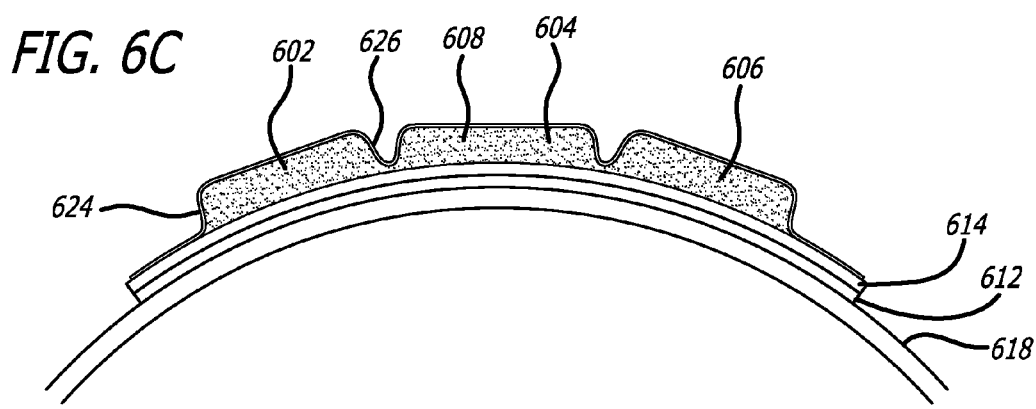
FIG. 6C is a cross-sectional view of the condition change multi-chamber label of FIG. 6A applied to a product housing.

An example multi-chamber structure is illustrated in FIGS. 6A-C. In FIGS. 6A-C, label 600 includes first blister 602, second blister 604, and third blister 606, each of which houses an indicator substance 608. More or fewer than three blisters can be used and in some embodiments, each blister can contain the same or a different indicator substance. In one embodiment, all blisters are connected. Before use, label 600 is attached to a liner 610 with an adhesive 612 applied to bottom layer 614. Between each adjacent blister is a groove 616. As stress is applied to label 600, for example by placing the label 600 on a cylindrical product housing 618, first edge 620 and second edge 622 of each blister stretch in the z-spring direction thereby creating first tensioned edge 624 and second tensioned edge 626. Likewise, each groove 616 expands in the v-string direction thereby relieving stress and allowing each blister to hold its shape.

Multi-chamber structures as described herein have walls between chambers, and the walls between the chambers act to hold the outer surface away from the bottom of the container. A similar effect could be done with pillars formed in the top film.

The condition change labels described herein can be sterilized by conventional methods without degrading or otherwise damaging the freeze indicator. Convention sterilization methods can include, but are not limited to sonication, gamma radiation, sterilization, autoclave, and the like.

The condition change labels described can be processed thorough existing processing lines without an impact on the speed of production or at substantially the same speed. Any modification to the processing line can be within the range of setup adjustment. For example, an existing processing line can label product housings at a rate of greater than about 80%, greater than about 90%, greater than about 95%, greater than about 96%, greater than about 97%, greater than about 98%, greater than about 99% of the speed of general labeling.

The condition change labels described herein can be used with high speed application machinery to label product housings. There are several areas in the process of supplying condition change labels and applying them to product housing with an automated machine where the container's flexibility can be important.

Figure 7:
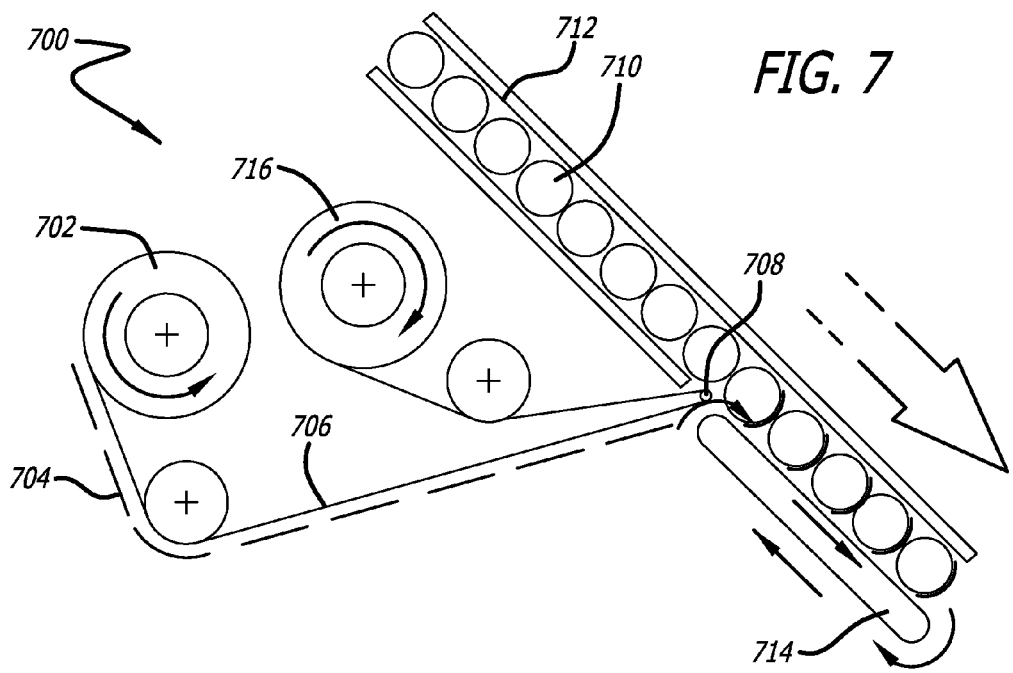
FIG. 7 is an example system for applying condition change labels as described herein.

FIG. 7 illustrates an example of a label applicator system using self-adhesive condition change labels supplied in roll form on a release liner. The system 700 includes a roll 702 of condition change labels 704 on a release liner 706. Roll 702 is counter clockwise rotated in order to unwind the roll. The release liner including labels is directed to and around a turn bar 708 adjacent to product housings 710 migrating down line 712. As labels are dispelled from the release liner 706 and stuck to product housings 710, a product housing rotator 714 can spin the product housings 710 in a clockwise direction to help adhere labels 704 to product housings 710. Release liner 706, now devoid of labels, is collected on a take-up spool 716. The various details of this system will be described below.

In some embodiments, if the labels are provided in self-adhesive roll stocks, they may need to be thin and/or flexible to remain on the liner through the feeding line and guide rolls.

Further, at the point of application, point 718 in FIG. 7, label 704 can be suitably stiff so that as the liner moves around turn bar 708 the label will release from the liner 706 and make contact with a product housing 710. A turn bar 708 can have a radius of about 1 mm. Immediately thereafter label 704 must be suitably flexible to conform to product housing 710 and attach to it. Further, label 704 can also have a suitably low stiffness so that it will not have an induced bending stress when it conforms to product housing 710 that induces adhesive creep and eventual partial or complete label detachment (wrinkling and flagging).

In some embodiments, in order to use condition change labels, they can be both adequately flexible and adequately stiff to adhere to the product housing with substantially no flagging.

The stiffness S, of a web or sheet of condition change labels can be calculated from the modulus of elasticity E, and the thickness d, using the relationship:

$$S = \frac{Ed^2}{12}$$

Stiffness is directly proportional to thickness cubed. For example, the stiffness of a film 20 μm thick is 8 times that of film of the same material that is 10 μm thick. Thinner films however are weaker and therefore may be more difficult to process, or have other drawbacks.

The modulus of elasticity and calculated stiffness for some materials used as labels for vials and other small diameter items, are estimated in Table 1.

TABLE 1

Modulus and stiffness of various label materials

| Material | $MD^2$ Modulus of elasticity MPa | Thickness μm | $MD^2$ Stiffness mN · m | Source |
| --- | --- | --- | --- | --- |
| PHARMAGLOSS ® 65 gsm coated paper (~6% H₂O)[1] | 2000 | 62 | 0.046 | Ahlstrom |
| PRIMAX ® 250 (white OPP)[3] | 800 | 62 | 0.016 | Fasson |
| LABELYTE ™ 65 (white OPP) | 800 | 67 | 0.020 | Exxon Mobil |
| LABELYTE ™ 19 (clear OPP) | 1800 | 19 | 0.001 | Exxon Mobil |
| Oriented PET | 3600 | 50 | 0.037 | DuPont Teijin |

[1]The modulus, & therefore stiffness, of paper varies inversely with moisture content.
[2]MD = machine direction
[3]OPP = oriented polypropylene The stiffness range that is functional for automated label application to small diameter items is comparatively wide. However, as the relationship between stiffness and thickness is cubic, the limits on the latter can be more restrictive.

Minimum stiffness for the condition change labels described can be determined from the stiffness needed to transfer them from the release liner to the vial during the automated process. A simple mechanism for removing self-adhesive die cut labels from a release liner is practiced with self-adhesive labels like postage stamps on rolls.

Figure 8A:
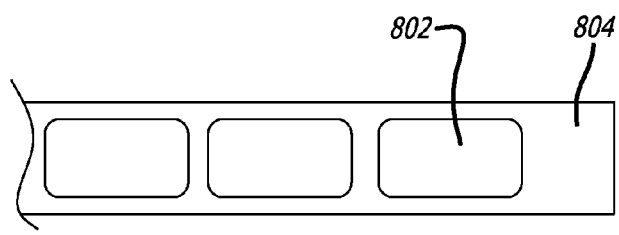
FIGS. 8A-B illustrate multiple condition change labels on a continuous liner.
Figure 8B:
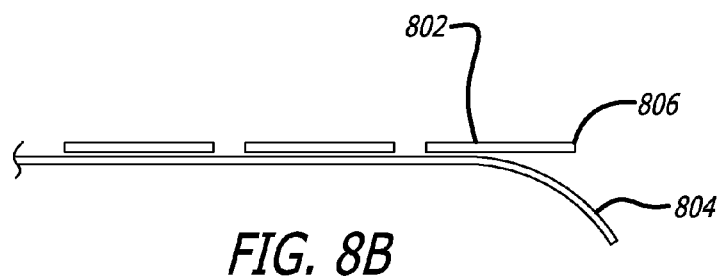

Such a process is illustrated in FIGS. 8A-B. FIG. 8A illustrates a series of labels 802 disposed on a continuous liner 804. As illustrated in FIG. 8B, as the labels reach a point when release liner is removed, for example, by a turn bar, the labels are stiff enough to be removed from liner 804 without external input. Edge 806 of label 802 detaches so it can be totally removed and applied to a product housing. The separation happens because the label tends to resist the bending and the adhesive is only weakly held by the liner.

Figure 9A:
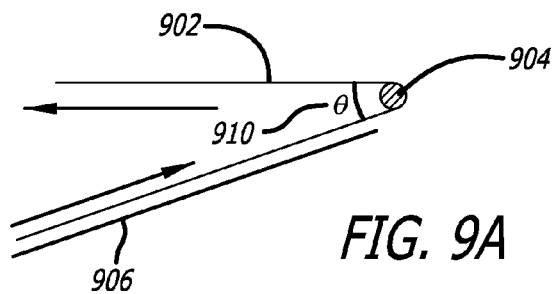
FIGS. 9A-D illustrate a continuous liner traversing at a turn bar and a condition change label's properties around that turn.
Figure 9B:
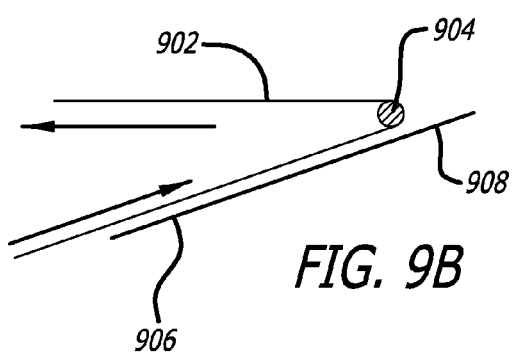
Figure 9C:
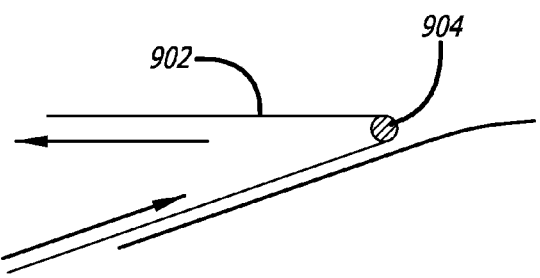
Figure 9D:
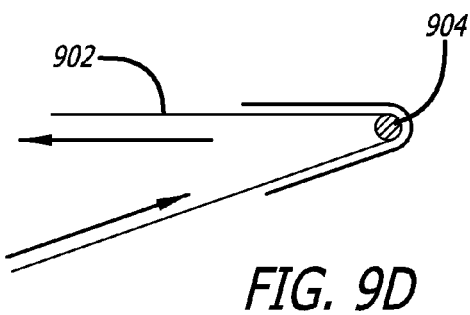

When labels are machine-applied in high volume, it may be desirable to use the lightest weight material available for economic benefit. Such materials are typically thinner than hand-applied labels, are less stiff, and so need to be bent through a much tighter angle to get release. As illustrated in FIGS. 9A-D, this can be done by wrapping release liner 902 around a small diameter turn bar 904. First as liner 902 advances, a label 906 approaches turn bar 904 (FIG. 9A). Then, as liner 902 advances further, label 906 detaches at leading edge 908 and begins to protrude beyond turn bar 904 (FIG. 9B). As liner 906 advances further label 906 continues to detach (FIG. 9C). In one embodiment, if the conditions are not appropriate for release, label 906 will remain with liner 902 and proceed around turn bar 904 (FIG. 9D).

The wrap angle around turn bar 904 can vary depending on the stiffness of label 906. For example, angle 910, defined as the remainder when the wrap angle is subtracted from 360 degrees, can be an angle such as, but not limited to, about 270 degrees, about 280 degrees, about 290 degrees, about 300 degrees, about 310 degrees, about 320 degrees, about 330 degrees, about 340 degrees, between about 270 degrees and about 340 degrees, between about 280 degrees and about 330 degrees, between about 290 degrees and about 320 degrees, at least about 270 degree, less than about 340 degrees, less than about 330 degrees, less than about 320 degrees, or less than about 310 degrees.

Turn bar 904 can be a cylinder or it can be a bar with a rounded end which can also have a very small radius. Turn bar 904 can also have a very small radius. A small radius can be about 1 mm, about 2 mm, about 3 mm, about 4 mm, about 5 mm, about 6 mm, about 7 mm, about 8 mm, about 9 mm, about 10 mm, between about 1 mm and about 5 mm, between about 1 mm and about 10 mm, between about 1 mm and about 2 mm, between about 1 mm and about 6 mm, at least about 0.1 mm, less than about 10 mm, less than about 5 mm, or less than about 2 mm.

This feeding behavior can be the basis for high-speed labelers and label machines for the application of self-adhesive labels to many items including cylinders such as bottles, syringes, jars, tubes and vials.

Figure 10A:
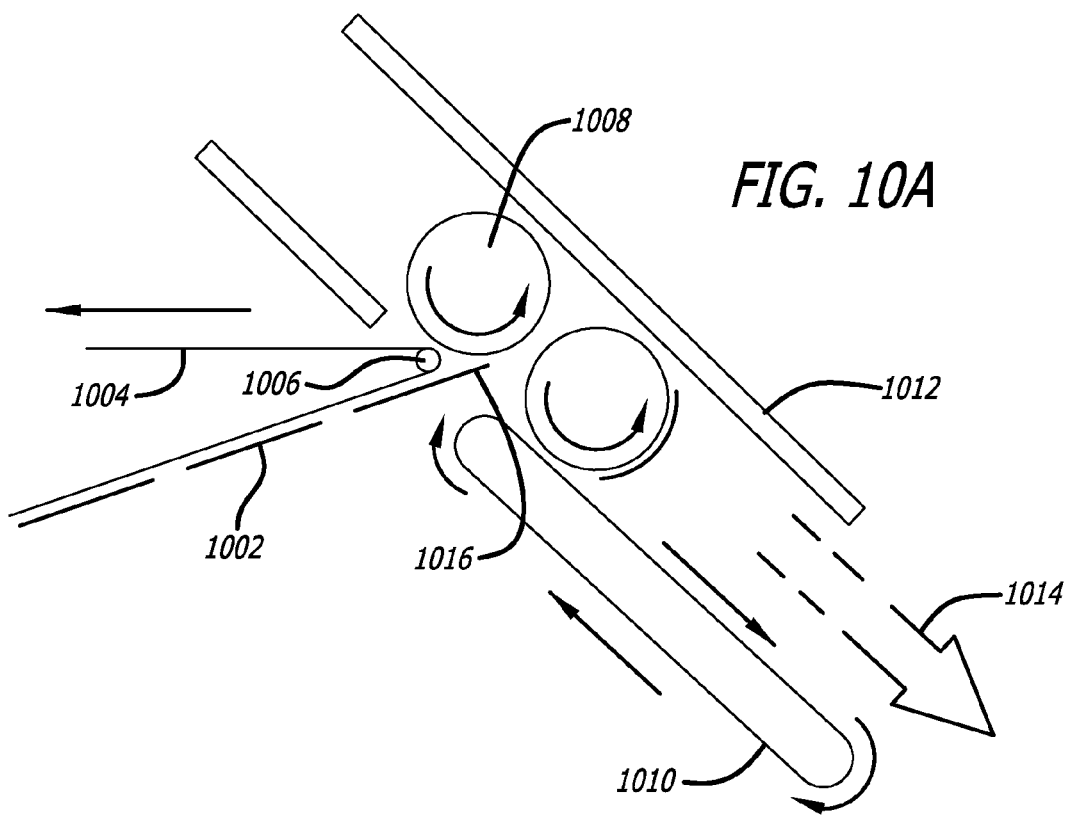
FIGS. 10A-B illustrate an example machine for applying labels at high speeds.
Figure 10B:
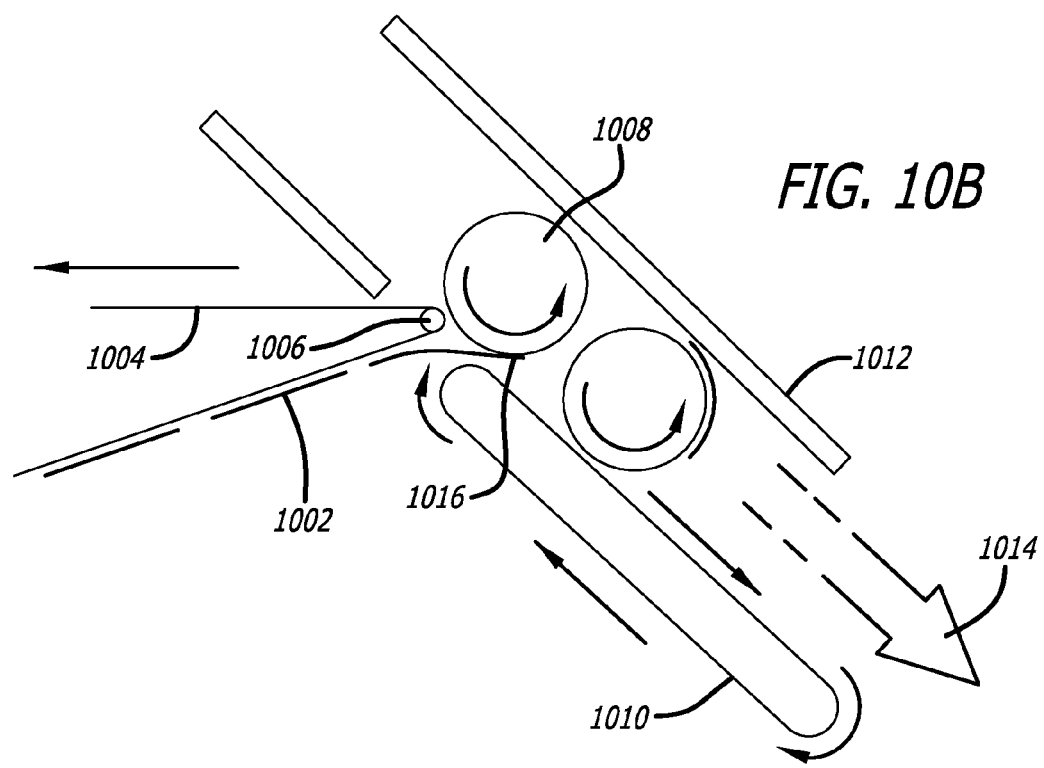

As illustrated in FIGS. 10 A-B, labels 1002 can be supplied as a roll, which can be held on an unwind station (not illustrated, but see FIG. 7 as an example). A continuous liner 1004 can be threaded from the unwind station, through the machine, around turn bar 1006, and to a take up winder (not illustrated, but see FIG. 7 as an example). Labels 1002 proceed along the outside of turn bar 1006. Turn bar 1006 is situated very close to the path of vials 1008 and has a small radius as described above.

In some embodiments, vials 1008 can be rotated as they pass through the machine, with assistance from a rotating band 1010 that is moving at a speed greater than the actual velocity of the vials. A stationary bar 1012 can be on the other side of the vial. The effect of rotating band 1010 and stationary bar 1012 is to roll vials 1008 forward and through the device. Labels 1002 are advanced in synchronization with vial movement 1014, one label for each vial. A leading edge 1016 can pass turn bar 1006 in between two adjacent vials, and if all factors are within the appropriate ranges, label 1002 will detach from continuous liner 1004.

As vials 1008 progress label 1002 extends further from liner 1004 until it and vial 1008 meet. The adhesive then attaches to vial 1008 and label 1002 moves in concert with it until it is fully detached from liner 1004. Vial 1008 is also rotating between stationary bar 1012 and rotating band 1010, so pressure is being applied to label 1002 to fix it firmly to the vial's surface.

Label release from the liner requires it to resist the bending force as the liner begins to bend around the turn bar. The resisting force can be solely from the stiffness of the label. The bending force can then be directly dependent upon the bond strength between the adhesive and the liner, and upon the radius of the bend around the turn bar. The label will fail to release if its stiffness is lower than the adhesive force.

In some embodiments, the condition change labels can be made with an adhesive of similar strength, a liner of similar thickness and release, and a facestock of similar stiffness.

Maximum stiffness for the condition change labels described can be determined by an ability to conform to the surface of the product housing or vial and remain there. Pressure sensitive adhesives (PSAs) can be used to hold the label to a vial. PSAs are fluid and may flow under stress. This is called adhesive creep. There can be a maximum force for any combination of materials and adhesive where there is no flow or creep.

Because of its stiffness, a flat bottom layer or substrate can require a force to bend, and to keep it in a bent position. For a label on a vial, if the adhesive strength exceeds the straightening force, there is no movement. But if the adhesive is weaker than the straightening force, creep occurs. As the force is concentrated at the ends of the label these will slowly lift away from the vial thereby resulting in flagging.

Figure 11A:
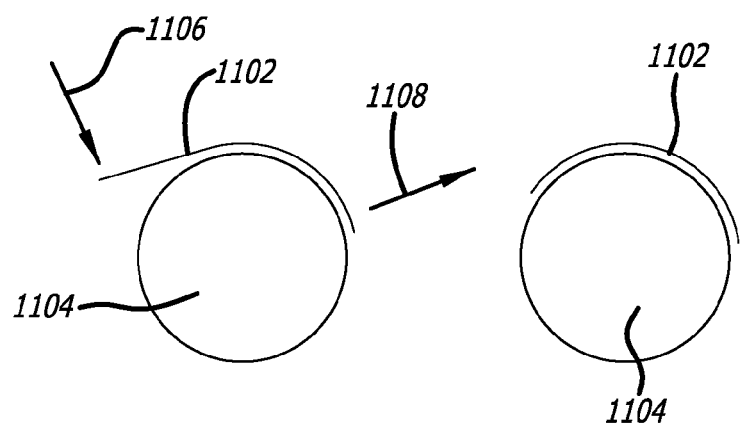
FIGS. 11A-B illustrate thickness properties of condition change labels when applied with different thicknesses to a cylindrical product housing.
Figure 11B:
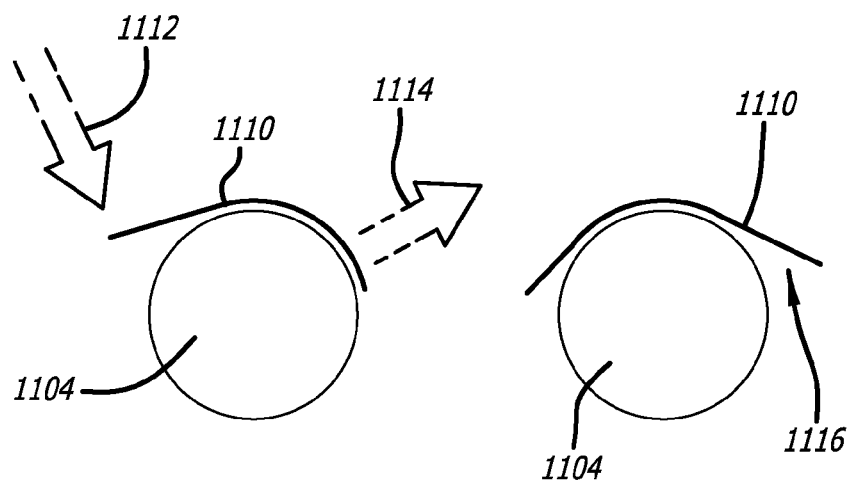

FIGS. 11A-B illustrate the effect of label thickness, and possible flagging as a result of a label that is too thick. FIG. 11A shows thick label 1102 being attached to vial 1104. If a force 1106 is applied to label 1102 as it is applied, the adhesive will hold label 1002 and prevent the stiffness response force 1108 from causing flagging. Conversely, in FIG. 11B, a thicker label 1110 is applied to vial 1104. A larger force 1112 is required to apply thicker label 1110 to vial 1104. However, here, the larger stiffness force 1114 can overcome the holding power of the adhesive and may cause flagging 1116.

Materials suitable for high speed application to small diameter vials, and which do not exhibit flagging when applied with permanent adhesives, include OPP of about 65 μm, 62 μm coated paper, and 50 μm PET (see Table 1). They all have calculated stiffness values of between about 0.03 mN·m and about 0.05 mN·m.

Stiffness values for other materials used to make condition change labels, are estimated in Table 2.

TABLE 2

Modulus and stiffness of various packaging films

| Material | MD Modulus of elasticity MPa | Thickness μm | Stiffness mN · m | Source |
|---|---|---|---|---|
| Biaxially Oriented Polyester | 3600 | 50 | 0.038 | DuPont Teijin |
|  | 3600 | 100 | 0.30 | DuPont Teijin |
|  | 3600 | 12 | 0.00052 | DuPont Teijin |
| Polychlorotrifluoroethylene | 1450 | 23 | 0.0015 | Honeywell ACLAR ® |
| Tempered Aluminum Foil | 69000 |  |  | Morris - DuPont |
| LDPE | 220 | 50 | 0.0023 | Morris - DuPont |
| PVC | 3200 | 175 | 1.4 | Klockner |

One of these materials, 100 μm polyester film, with standard label adhesives has shown flagging in experiments in which it was applied to a 12 mm diameter glass vial. It has a stiffness of about 0.3 mN·m which may be too high for the use under these circumstances. Similarly, 175 μM PVC, a common blister pack forming film, is even more rigid, and may not be suited for these circumstances.

In one embodiment, a film for the manufacture of a long life indicator is polychlorotrifluoroethylene (PCTFE), available from Honeywell Specialty Materials, Morristown, N.J. as ACLAR®. This material is transparent, tough and has excellent barrier properties toward water and water vapor. The elastic modulus of 23 μm thick ACLAR® 90Rx is about 1450 MPa and it has a stiffness of about 0.0015 mN·m. As such, in some embodiments, ACLAR® can be used to form at least a portion of a condition change label.

Solid metals and alloys are frequently soft when made by solidifying a melt. They can be stiffened and hardened by tempering, for example by rolling into foils at temperatures below the metal's recrystallization temperature (also know as cold working). Tempered metals can be softened or annealed by holding at temperatures above the metal's recrystallization temperature. Aluminum foil for example, is a desirable material to be used in the bottom layer of a condition change indicator because it is a total gas and liquid barrier. Aluminum foil is often produced by cold rolling, in which case it is tempered and therefore comparatively hard, stiff and resistant to stress relaxation. Cold rolled aluminum foil can be converted to soft foil by annealing, so that it is in comparison less stiff, more ductile and demonstrates stress relaxation so it may be useful for the indicator of the current disclosure.

In some embodiments, the indicator stiffness may have a minimum value, which may help it to be released from the liner, and a maximum value to help avoid flagging at different times and over different timescales. For example, a 25 mm long label being applied at a rate of 300 per minute by an automated label applicator is unsupported for no more than 10 mm, or not longer than 10 ms. But high stiffness is undesirable for the life of the labelled items, which may be days, or weeks, or months or years. It is therefore advantageous to utilize substrates that when bent, as around a vaccine vial, lose stiffness over time. This phenomenon is called stress relaxation. Paper is well known to demonstrate substantial stress relaxation over time, but paper is typically porous and so unsuited for use in an indicator containing fluids. Polypropylene exhibits moderate stress relaxation but biaxially oriented polyester is comparatively resistant to stress relaxation. For this reason, polypropylene might be preferred over biaxially oriented polyester for vaccine vial labels.

In one embodiment, the indicator substance can be a liquid-based freeze indicator. Such an indicator can be prepared from a laminate of two films, a film and a foil, or a film and another film/foil laminate, with a cavity or blister in the first to hold the liquid. Laminate stiffness is dependent upon the properties of the layers making up the laminate. An example of this principle is provided by rigid lightweight door panels, which are made from thin skins of veneer, bonded tightly to a core of rigid polymer foam. The structure has much greater stiffness than any of the individual parts, and also much greater than if the two layers of veneer are glued together, and the foam bonded to the surface of one. When higher modulus materials make up the outer plies of the laminate, the product is stiffer than when they are buried.

Figure 12A:
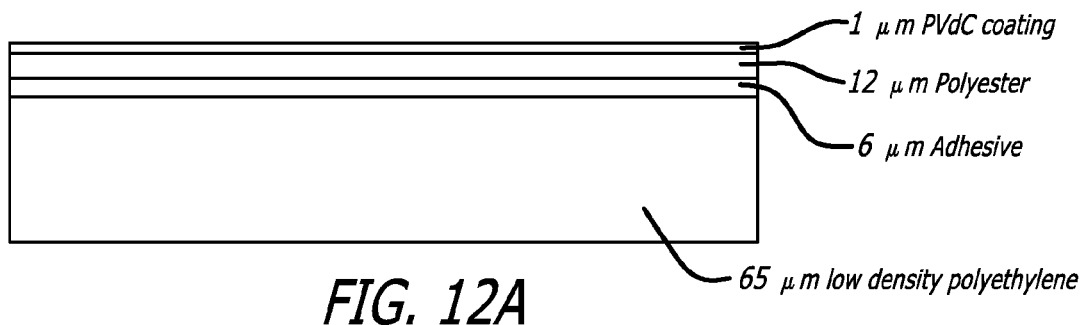
FIGS. 12A-B illustrate two example laminated condition change label structures.
Figure 12B:
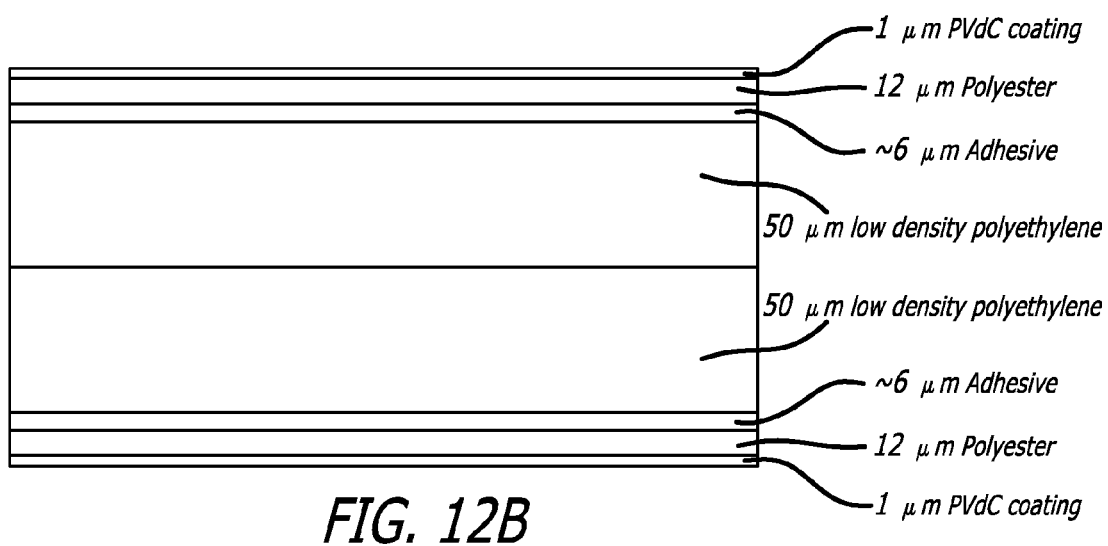

A material used for the manufacture of pouches and bags can be a film of 12 μm polyester (often coated with 1 μm of polyvinylidene chloride for barrier properties) bonded to a 65 μm low density polyethylene film, with about 8 μm of adhesive. This is illustrated in FIG. 12.

The modulus of polyester is about 3800 MPa compared to low density polyethylene at about 150 MPa. The stiffness of this structure is about 0.01 mN·m, which is suitable for use as a small vial label stock. When used for manufacturing pouches and bags, two sheets or webs of this laminate are used and brought together so that the polyethylene surfaces are in contact. These are conveniently bonded with heat to form a structure of total thickness about 140 μm.

The high modulus polyester films are at the outsides of the combined structure. The stiffness of this material is about 1.1 mN·m. Doubling the apparent thickness in this manner produced a stiffness response much greater than a factor of 8, because the high modulus components are at the surfaces. This is a desirable attribute for the majority of applications of this material which includes bags and stand up pouches, but may not be suitable in the design of a flexible material. In one example embodiment, a composite composed of 2 layers of 50 um thick PCTFE film laminated with 10 um of flexible adhesive has a stiffness of about 0.16 mN·m.

A modified stiffness measurement test was developed to meet the unique requirements of this application, such as samples too small to fit the standard devices, bending about much smaller radii, and non-linear responses of laminates of varied construction, especially when working with materials stressed beyond the plastic limit. The following description refers to FIG. 13.

Figure 13A:
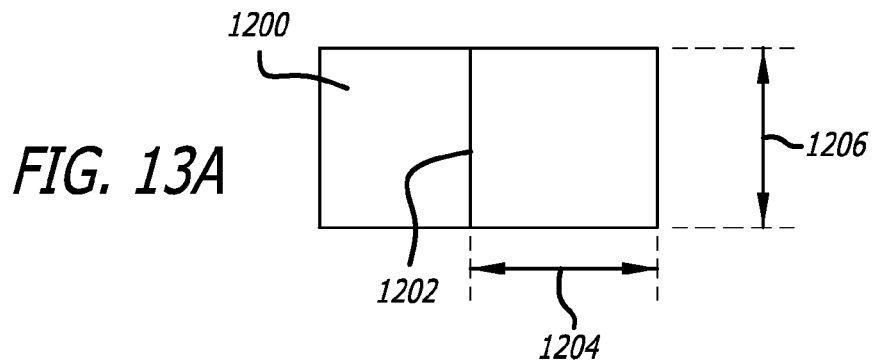
FIGS. 13A-C illustrate a method to measure the force required to bend a label around a cylindrical object.
Figure 13B:
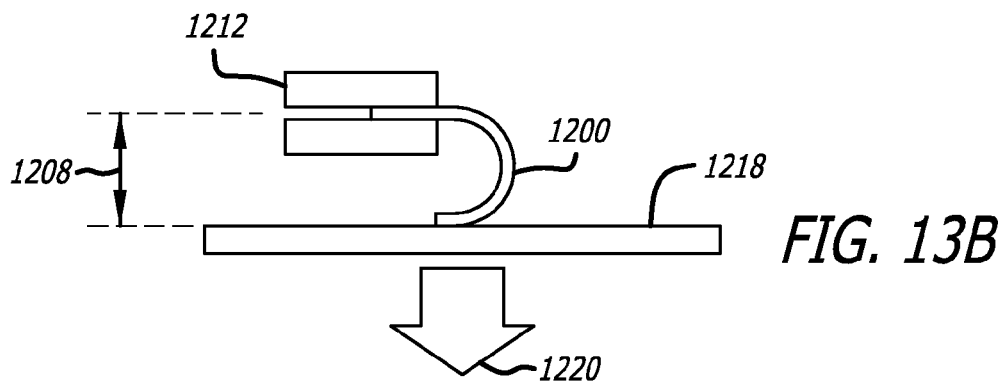
Figure 13C:
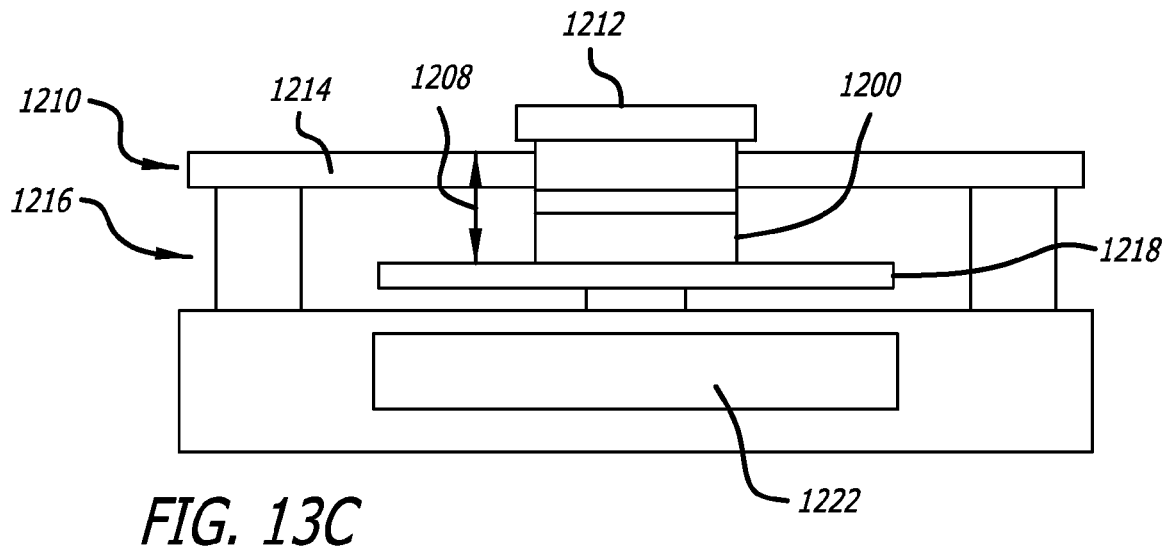

FIGS. 13A to 13C show the measurement of resistance to bending. The measurement of resistance to bending is made on rectangular samples 1200 of material of known width. A light pencil line 1202 is made a distance 1204 from one end. The distance 1206 is ½ the circumference of the container for which resistance to bending is desired. The length of the sample is about 2 cm longer than the distance 1204.

A tool 1210 is made from a clamp 1212 fixed to a rigid beam 1214. The sample is placed in the clamp 1212 with the clamp line aligned with the clamp. This assembly is placed above a top loading balance 1216 so the clamp 1212 is at the center of the balance pan 1218, and the distance between the clamp 1212 and the pan 1218 is equal to the diameter of the container. The top loading balance 1216 is first tared (set to read zero). The tool 1210 with the sample is lifted and twisted about 150° so that the sample end contacts the pan. The tool 1210 is then rolled back and positioned on the balance 1216 with the sample 1200 remaining in contact with the pan. The end of the sample 1200 is directly below the edge of the clamp 1212 so the bent sample approximates a semicircle. The force on the balance is displayed on the balance display 1222. It is recorded about 30 seconds after the load is applied. The value reported is the force per unit width, i.e., g/cm, for the intended semicircle diameter. Most measurements were made to replicate a 17 mm diameter vial so the distance between the clamp and the pan was 17 mm, and the clamp line was 26.5 mm from the end of the sample.

TABLE 3

Comparison of resistance to bending and stiffness calculated from modulus.

| Material | Force to wrap 17 mm vial (g/cm) | Thickness (μm) | Stiffness from Modulus |
|---|---|---|---|
| 115 μm PET Melinex ® 054 (1) | 11 | 115 | 5.0 |
| 67 μm PET MD Melinex ® 054 | 2.2 | 67 | 0.93 |
| 75 μm PET Melinex ® 505 (CD) | 2.6 | 75 | 1.3 |
| 200 ga (50 μm) PET DC628 (2) | 0.71 | 50 | 0.39 |
| Aclar ® SupRX900 PCTFE (3) | 0.01 | 23 | 0.02 |
| 2.0 mil Aclar ® UltrRx2000 PCTFE | 0.20 | 50 | 0.18 |

(1) Melinex is a product of DuPont Teijin Films, Wilmington, DE.
(2) DC628 is a product of Dunmore Corp., Bristol, PA,
(3) Aclar ® is a product of Honeywell Specialty Films, Morristown, NJ There is a direct relationship between the force to hold a semicircle of 17 mm and the stiffness calculated from the modulus.

The force to bend to 17 mm was measured for several label substrates, including vaccine vial label stocks. The results are shown in Table 4.

TABLE 4

Label stock resistance to bending to 17 mm diameter

| Material | Resistance to bending (g/cm) |
|---|---|
| Skyrol ® SW03 200 ga white polyester (1) | 0.94 |
| Raflatac 2.4 mil Hi D PP White polypropylene (2) | 0.78 |
| Raflatac 2.6 mil Hi D PP white polypropylene | 0.71 |
| Fasson Pharmagloss paper labelstock (3) | 0.76 |
| Spinnaker Pharmagloss paper labelstock (4) | 0.90 |
| Fasson Primax 150 white polypropylene (3) | 0.14 |

(1) Skyrol ® is a product of SKC, Inc. Covington, GA.
(2) UPM Raflatac, Inc. Mills River, NC;
(3) Avery Dennison Fasson Roll North America, Painesville, OH;
(4) Spinnaker Coating, Troy OH.

The primary vial label materials all have initial resistance to bending of from 0.7 to 1 g/cm. The range for materials that will perform satisfactorily will include this range. Primax 150 is much lower. It does not release readily during high speed application so its stiffness would be out side the range of materials expected to perform in a high speed vial label line that had not been modified for use with very low stiffness label stock.

The resistance to bending of two vial labelstocks was measured with a 10 mm diameter semicircular configuration. It is shown in Table 5.

TABLE 5

Resistance to bending to 10 mm diameter of vaccine vial label stock

| Material | Resistance to bending (g/cm) |
|---|---|
| Raflatac 2.4 mil Extra White polypropylene | 1.7 |
| Fasson Pharmagloss paper labelstock | 1.6 |

The force to hold the label to the vial has essentially doubled even though the diameter has been reduced by only 40%.

The 3-dimensional nature of the liquid container adds structural rigidity to mass produced small flexible containers such as pouches and sacs. Because the container is too rigid to wrap a small diameter item, there has been no demand for the rest of the indicator to be suitably flexible for this use. Instead, the indicators can utilize materials used for the method of manufacture. For example, the ATI item is a pouch or sac made from two layers of a laminate of a barrier coated 13 μm polyester film and a 50 μm polyethylene film. The thickness of the laminate is about 125 μm. The item described in U.S. Pat. No. 7,343,872 is made on a blister pack machine from a laminate of polyvinyl chloride and polychlorotrifluoroethylene (ACLAR®) with a thickness of at least 175 μm, and then combined with an aluminum foil of at least 25 μm. This laminate is even stiffer than the polyester/polyethylene laminate. Materials that are suitable for labels intended to be applied to small diameter vials can include PHARMAGLOSS™, a 65 g/m² paper from Ahlstrom, Helsinki, and PRIMAX® 250 a 65 μm oriented polypropylene from the Fasson Division of Avery Dennison Corp., Painesville, Ohio. Both of these materials have much lower stiffness values than the laminates of the existing freeze indicators.

Therefore, to produce a freeze indicator with a thin container of a fluid with intense visual indication and that can be made, processed and utilized like a pressure sensitive label, it may be useful to construct the indicator itself and the container for the fluid from materials that when combined have low stiffness.

In some embodiments, condition change labels can be provided in single lane rolls ready for use in label applicators. The single lane roll can be unsupported, that is, without a flange, side plate or spool. Rolls of this structure can be wound only if they are laterally stable, and do not by themselves telescope, which renders them unusable in most applicators. Telescoping may occur when one layer of web moves laterally relative to its neighbors. Stable rolls do not permit this movement, first because they are wound so with a moderate level of tension, second because there is friction between the top of one layer and bottom of the next. Additionally, labels can be essentially flat items depending on the design of the container.

In some embodiments, the condition change label is not the freeze indicator produced by ATI under the name FREEZE CHECK™ or the freeze indicator described in U.S. Pat. No. 7,343,872. However, in some embodiments, a FREEZEmarker® freeze exposure indicator can be used as in a condition change label.

Another deficiency of an indicator such as a FREEZE CHECK™ indicator is its thickness, which limits the number of that can be wound into rolls with industry established maximum diameters. The difference in number of indicators in a roll of fixed diameter is directly related to the difference in thickness. A roll of paper labels for vials usually contains at least 1,000 labels. A comparable sized roll with 1 mm thick indicators may contain no more than about 110 labels. This may be unattractive to the operators of automated equipment because the frequency of replacing rolls becomes excessive. Therefore, miniaturized condition change labels as described herein can be very shallow and make a minimal contribution to thickness.

For a small vial the indicator must itself be small relative to the surface area of the vial as the surface is covered to a large degree by the label which has a large amount of information required for the item to comply with regulations. An ideal size can be a little more than the minimum required for the visual indicator plus the sealing area surrounding it. A useful minimum size for a circular visual indicator can be 4 mm width or diameter. With a sealing distance of 2 mm on all sides, the final diameter may be only about 8 mm. This can be accommodated on many vials.

Some commercially available indicators, such as the I-STRIP™ from Timestrip and the FREEZE CHECK™ from ATI both have width and length dimensions much greater than 8 mm, or even 18 mm, so both may be unsuited for attachment to pharmaceutical vials as described herein. In some embodiments, the condition change label does not include an I-STRIP™ or a FREEZE CHECK™ indicator.

Any suitable indicator substance can be used with the indicators described herein. Some examples of useful indicator substances are described in U.S. Pat. Nos. 8,430,053; 6,957,623; 8,128,872; 7,343,872; 7,571,695; and 8,122,844, all of which are incorporated for reference for all disclosure related to freeze indicator substances or other kinds of indicator substances, as well as U.S. patent application Ser. No. 13/968,895, filed Aug. 16, 2013 and 61/839,658, filed Jun. 26, 2013, both of which are incorporated for reference for all disclosure related to freeze indicator substances or other kinds of indicator substances.

Typically, a freeze indicator can include a two or three-phase emulsion or dispersion (referred to herein as an "indicator dispersion") that is affected by freezing. For example, freezing can cause coagulation or coalescence of a dispersed phase. As a result of the coagulation or coalescence, the appearance of the indicator substance can change. This change may have to do with the physical or optical properties of the phases themselves, such as a change in light scattering of a dispersed phase, or transfer of a material, such as a colorant or an opacifying agent, from one phase to another.

An indicator substance may contain a reactive agent that changes color upon reaction. For example, a dispersed phase may comprise two or more discreet types of particles or droplets. A first type of particle or droplet could contain a first reactive agent, and a second type of particle or droplet could contain a second reactive agent. The first and second reactive agent can react with one another to produce a change in appearance, such as a color change. Thus, when the different types of particles or droplets in the dispersed phase coalesce or coagulate upon freezing, the first and the second reactive agent can react to produce the change in appearance, such as a color change, that can alert a user that a freezing event has occurred. In some embodiments, an indicator substance can comprise water and a hydrophobic material.

Some indicator substances can comprise a colorant. A colorant in an indicator dispersion may be of any useful color, such as red, orange, yellow, blue, green, violet, or black. For indicator dispersions that are water-in-oil (w/o) emulsions, water-in-oil-in-water emulsions (w/o/w), or oil-in-water-in-oil (o/w/o), a dispersed aqueous phase can contain a colorant that is water-soluble. For example, a colorant may have a water solubility of at least about 10 mg/mL, at least about 50 mg/mL, or at least about 100 mg/mL. It may also be helpful for the colorant to have a substantially greater solubility in water than in oil. For example the colorant can be at least 2 times, at least 5 times, at least 10 times, at least 50 times, at least 100 times, at least 1000 times, or at least 10,000 times more soluble in water than in oil by weight. It may also be helpful for a water-soluble colorant to have a low oil solubility. Low oil solubility may avoid or reduce possible migration of the colorant into an oil phase, which may cause premature coloration of the indicator dispersion. For example, the colorant may have a solubility less than about 10 mg/mL, less than about 1 mg/mL, or less than about 0.1 mg/mL. Examples of suitable colorants include basic dyes such as methylene blue, malachite green, etc.; acid dyes such as Naphthalene Red EA, Naphthalene Scarlet 4R, Naphthalene Orange G; Crystal Violet, etc.; acid-base indicators, such as phenolphthalein, gentian violet, leucomalachite green, thymol blue, methyl yellow, bromophenol blue, congo red, methyl orange, bromocresol green, methyl red, azolitmin, bromocresol purple, bromothymol blue, phenol red, neutral red, napthophthalein, cresol red, thymophthalein, etc. Basic dyes can have extinction coefficients an order of magnitude higher than acid dyes.

For o/w, o/w/o, or w/o/w dispersions or emulsions, a dispersed oil phase may contain a colorant that is soluble in oil or hydrophobic solvents. For example, a colorant may have a solubility of at least about 10 mg/mL, at least about 50 mg/mL, or at least about 100 mg/mL in oil or a hydrophobic solvent. It may also be helpful for the colorant to have a substantially greater solubility in water than in oil or a hydrophobic solvent. For example the colorant can be at least 2 times, at least 5 times, at least 10 times, at least 50 times, at least 100 times, at least 1000 times, or at least 10,000 times more soluble in water than in oil or a hydrophobic solvent by weight. For dispersed oil phases containing a colorant, it may also be helpful for the colorant to have a low water solubility. Low water solubility may avoid or reduce possible migration of the colorant into an aqueous phase, which may cause premature coloration of the indicator dispersion. For example, the colorant may have a solubility of less than about 10 mg/mL, less than about 1 mg/mL, or less than about 0.1 mg/mL in water.

An indicator dispersion may contain any useful amount of a colorant. The proportion of colorant can be decreased to reduce color before a temperature condition, such as a freezing event, is met, if present, or can be increased to increase color after a temperature condition, such as a freezing event, is met, if desired. In some embodiments, the amount of colorant in the indicator dispersion is at least about 0.005%, at least about 0.002%, at least about 0.01%, at least about 0.05%, or up to about 0.05%, up to about 0.1%, up to about 1%, about 0.01% to about 1%, about 0.01% to about 5%, or about 0.01% to about 10%, based upon the weight of the colorant in the total weight of the dispersion.

An aqueous phase can include any suitable aqueous liquid such as water. One or more water-miscible liquids having a melting point higher than that of water may optionally be included in the aqueous phase. For example, deuterium oxide (D2O), deuterated water (HOD), or a mixture of deuterium oxide and deuterated water, may be combined with or substituted for light water. In some embodiments, an aqueous phase may be 90% to nearly 100% deuterated water and/or deuterium oxide. The melting point of an aqueous phase may be adjusted to correspond to a temperature condition to be monitored. Adjustment of the melting point may be carried out by suitable selection of aqueous ingredients and their proportions.

An oil or hydrophobic phase can comprise any suitable hydrophobic material, such as a hydrophilic solid or liquid, including a liquid that is a water barrier, or tends to repel or not absorb water, or has a lack of affinity for water. In some embodiments, the hydrophobic liquid may have a water solubility that is less than about 10%, less than about 1%, less than about 0.01%, less than about 0.001%, or less than about 0.0001%. It may also be helpful to have a hydrophobic material that is unreactive with other components of the indicator dispersion, including the colorant, or with any housing or containment material that the temperature condition indicator may employ to contain the indicator dispersion in the context of the indicator dispersion.

Use of a hydrophobic material having a relatively high refractive index, such as greater than about 1.45 or about 1.5, can help provide a more opaque, or lighter colored dispersion in some cases. Vegetable oils, such as olive oil or sunflower oil, may have refractive indexes of about 1.47. Mineral oil has a refractive index of about 1.48. Hydrogenated terphenyl oils have a refractive index of about 1.52.

Some examples of useful oils or hydrophobic liquids include hydrocarbons such as heptane, octane, nonane, decane, undecane, dodecane, tridecane, hexadecane and the like, either linear or branched; aromatics such as toluene, xylene, etc., mineral oil, terphenyl oils, etc.; esters, including vegetable oils, such as soybean oil, cottonseed oil, linseed oil, rapeseed oil, castor oil, sunflower oil, olive oil, kernel oil, peanut oil, corn oil, canola oil, coconut oil, hazelnut oil, avocado oil, almond oil, arachis oil, safflower oil, maize oil, soybean oil, caraway oil, rosemary oil, peppermint oil, eucalyptus oil, sesame oil, coriander oil, lavender oil, citronella oil, juniper oil, lemon oil, orange oil, clary sage oil, nutmeg oil, tea tree oil, etc., liquid fatty acid esters, such as liquid fatty acid esters of lauric acid, palmitic acid, stearic acid, etc.; silicon oils, such as siloxanes, polysiloxanes, cyclopolysiloxanes, dimethicone, etc.; heteroatom functionalized hydrocarbons, including haloaromatic compounds such as halogenated aromatic compounds, phenols, alkoxyaromatics, perflouroalkanes, etc. A mixture of two or more oils can also be used. One suitable terphenyl oil is available under the product code MCS 2811 from Solutia, St. Louis Mo. Some further suitable hydrophobic liquids are described in Taylor U.S. Pat. No. 8,430,053, which is incorporated by reference herein for all it describes related to hydrophobic liquids.

Use of a water-in-oil-in-water emulsion may allow a reduced amount of oil to be used as compared to temperature condition indicators based on an oil-in-water emulsion. Low oil or hydrophobic phase may provide some advantages for some indicator compositions. For example, a lower oil temperature condition indicator may have better response characteristics, such as more consistent mixing of the active phase and the base phase at a given temperature. Higher oil may in some instances adversely affect heat conductivity or may impede the spread of crystallization through the aqueous phases. In some embodiments, the hydrophobic phase may be about 0.1% to about 40%, 0.5% to about 20%, about 0.1% to about 10%, or about 1% to about 5% of the total weight of the indicator dispersion.

One method of reducing hydrophobic liquid or oil content may be to have a high load of a dispersed aqueous phase in an intermediate oil or hydrophobic phase of a w/o/w emulsion. For example, the weight ratio of dispersed aqueous phase to hydrophobic phase may approach or even exceed 1:1 (aqueous active phase:hydrophobic phase), such as at least about 1:10, at least about 1:5, at least about 1:4, at least about 1:3, at least about 1:2, at least about 1:1, up to about 1:2, about 1:1, about 2:1, about 1:5 to about 2:1, about 1:4 to about 2:1, or about 1:2 to about 2:1.

For freeze indicators, an indicator dispersion may include an ice nucleant to help overcome supercooling and provide a freeze response at a temperature closer to the melting point of the dispersion medium than would occur if the ice nucleant is not present. An ice nucleant can reduce the effect of supercooling, elevate the freezing temperature of the active and/or aqueous base phase, and therefore of the indicator dispersion, and narrow the difference between the melting point of the freezing point of the indicator dispersion.

Useful ice nucleants include inorganic ice nucleants and proteinaceous ice nucleants derived from microorganisms. Some examples of useful inorganic ice nucleants include silver iodide, cold-precipitated silver iodide/silver bromide mixtures, and copper sulfide. An example of a useful proteinaceous ice nucleant is SNOWMAX™ Snow Inducer, a freeze-dried proteinaceous material available from Snomax International, Centennial, Colo. Some suitable ice nucleants are also described in Taylor U.S. Pat. No. 8,430,053, which is incorporated by reference herein for all it describes with respect to ice nucleants. Any useful amount of ice nucleant may be used, such as about 0.1% to about 5% or about 0.2% to about 2% by weight.

Freeze indicators that employ a proteinaceous ice nucleant can include a protein stabilizer in the indicator dispersion to stabilize the ice nucleant against thermal or other degradation, if desired. Some examples of suitable protein stabilizers include formaldehyde, glutaraldehyde (CHOCH$_2$CH$_2$CH$_2$CHO), and other dialdehydes having more than 10 carbon atoms. Some suitable protein stabilizers are also described in Taylor U.S. Pat. No. 8,430,053, which is incorporated by reference herein for all it describes with respect to protein stabilizers. Any useful amount of protein stabilizer may be used, such as about 0.01% to about 1%, or about 0.05% to about 0.5% by weight.

If desired, a biocide may be included in an indicator dispersion that employs a proteinaceous ice nucleant to prevent microbial spoilage. Certain protein stabilizers, for example glutaraldehyde and other dialdehydes, can also serve as biocides, when used in an effective concentration. Other biocides may also be used.

To help maintain the stability of the indicator dispersion, an indicator dispersion may include a dispersion stabilizer. Some examples of suitable dispersion stabilizers include surfactants, such as anionic surfactants, cationic surfactants, zwitterionic surfactants, non-ionic surfactants or combinations thereof. In addition to those described above, in some embodiments, surfactants can include fatty acid salts, linear alkyl benzene sulfonates, dialkyl phosphates, linear alcohol sulfates, alkylphenol ethoxylates, sulfonated alkylphenol ethoxylates, fatty acid ester ethoxylates, ethylene oxide propylene oxide block copolymers, fatty acid sulfonates, betaines, quaternary ammonium salts. In some embodiments, Span 80 (a non-ionic surfactant within HLB number of 4.3, also known as Arlacel 80 [1,4-anhydro-6-O-[(9Z)-9-octadecenoyl]-D-glucitol]) may be useful to stabilize the aqueous active phase in the hydrophobic phase. In some embodiments, Tween 80 (a non-ionic surfactant within our HLB number of 15, also known as polysorbate 80 [3,6-anhydro-2,4,5-tris-O-(2-hydroxyethyl)-1-O-{2-[(9Z)-9-octadecenoyloxy]ethyl]hexitol]) may be useful to stabilize the hydrophobic phase in the aqueous base phase. In some embodiments, the dispersion stabilizer may be sodium stearate, sodium dodecyl sulfate, ammonium lauryl sulfate, sodium laurel phosphate, betaine, lauryl amido propyl dimethyl betaine, dodecyl trimethyl ammonium chloride, benzalkonium chloride, sorbitan monolaurate, and oleyl alcohol.

In other embodiments, so called Pickering emulsifiers may be used either exclusively or in addition to those already delineated. These are solid particulates with appropriately modified surface chemistry. For example hydrophobically surface modified silica nanoparticles, such as Aerosil R972 (Degussa Corporation) and the like may be used to make an initial water-in-oil emulsion that is then converted into the w/o/w emulsion in a second step with a different surface modified particle. An example of such a particle is fumed silica whose surface has been modified by adsorption or chemisorption to give the right balance of hydrophilicity and hydrophobicity. Many different materials may be adsorbed onto the surface of appropriate particles including surfactants. Useful Pickering emulsifiers are not limited to silica particles. In fact, many different particulates, of any 3 dimensional shapes, such as spherical, platelet, irregular etc., may be used including, but not limited to colloidal alumina, colloidal yttria, colloidal zirconia, etc.

Other stabilizers may include water-soluble or water absorbing polymers such as poly(vinylpyrrolidone); polysaccharide derivatives, such as cellulose derivatives, including carboxymethylcellulose, hydroxypropylmethylcellulose, etc., hyaluronic acid derivatives, etc.; water-soluble acrylics, such as polyacrylic acid, polymethacrylic acid, etc.; polyethylene oxides; starches; guar; alginates; chitosan; etc. Any useful amount of dispersion stabilizer may be used, such as about 0.1% to about 10% or about 0.5% to about 5% by weight.

Some further dispersion stabilizers are also described in Taylor, U.S. Pat. No. 8,430,053 (Taylor '053), which is incorporated by reference herein for all it describes with respect to dispersion stabilizers. Any useful amount of dispersion stabilizer may be used, such as about 0.1% to about 10% or about 0.5% to about 5% by weight.

Optionally, if a dispersion stabilizer is present, an indicator dispersion may include a destabilizer to facilitate low-temperature destabilization of the indicator dispersion. A low-temperature destabilizer may promote or enhance coagulation of a freeze indicator dispersion at freezing temperatures, without unacceptably impairing the warm temperature stability properties of the dispersion. A low-temperature destabilizer can be a concentration-sensitive destabilizing or coagulating agent, for example, and ionic compound or compounds, or another suitable compound or compounds such as a high molecular weight compound. The destabilizing action of the low-temperature sensitive destabilizer can depend upon the concentration of the destabilizer aqueous liquid. Generally, although not necessarily, a temperature stabilizer also present with a low-temperature destabilizer is employed.

Examples of low-temperature destabilizers include salts, such as inorganic salts, monovalent salts, and multivalent salts. Some examples of suitable salts include chlorides, sulfates, nitrates, and carboxylates of potassium, sodium, ammonium, calcium, magnesium, and mixtures thereof.

Other materials that can be employed as low-temperature destabilizers include high molecular weight cationic, anionic, zwitterionic and uncharged polymers having a weight average molecular weight of about 1000 Da to about 100,000 Da. Some examples of polymers useful as low-temperature destabilizers include polyacrylamides, polyvinyl alcohols, polyvinyl pyrrolidones, and poly acrylic acids. Some useful polymers may be water-soluble, and two more such polymers may be employed in a given indicator dispersion. Some suitable the stabilizers are also described in Taylor '053, which is incorporated by reference herein for all it describes with respect to stabilizers.

A low-temperature destabilizer, if employed, may be selected for its compatibility with a particular dispersion stabilizer present in an indicator dispersion. To illustrate, a polymeric destabilizer employed with an ionically stabilized indicator dispersion can carry an opposite charge to the charge carried by the indicator dispersion. For example, the cationic polymer including quaternary ammonium segments can be used to destabilize a stabilized indicator dispersion that employs an anionic stabilizer.

In some embodiments, an indicator dispersion may comprise, or consist essentially of, one or more aqueous phases, one or more hydrophobic or oil phases, and one or more optional components, wherein each optional component is a colorant, a solute, a surfactant, an acid, a base, a buffer, an ice nucleant, a protein stabilizer, the dispersion stabilizer, a low-temperature destabilizer, or a biocide.

In some embodiments, an indicator dispersion may comprise a mixture of water, latex, nucleating agent, and stabilizing agents which is translucent prior to exposure to a threshold temperature, such as a freezing temperature, and is transformed upon being subjected to the threshold temperature to render a substantially consistent opaque material thus precluding visibility therethrough and thereby providing a sure visual sign that the indicator has been subjected to the predetermined temperature.

The latex includes particles having a diameter of less than about 0.05 microns and is present in the material in an amount of from about 5 to 35% or about 15 weight %. The nucleating agent is present in the material in an amount of from about 0.01 to 1.0 weight percent, with a preferred weight percent of 0.025 and includes ice nucleating agents (INA) which contain a molecular structure to attract the water and which upon reaching the threshold temperature interact with the latex to form the opaque material. Also included in the latex is a material designed to thermally stabilize the INA. This material chemically locks the molecular structure of the INA so that it does not change with time and/or elevated temperature. The stabilizing material can be, for example, one in the family of dialdehydes that includes glyoxal, glutaraldehyde, and terephthalaldehyde.

The latex material can be formed from organic solid particles of a polymeric resinous material (e.g., rubber) in water. Both natural and synthetic latexes may be employed, provided the chosen latex material provides the functionality of being irreversibly transformable when combined with the ice nucleating active (INA) microorganisms nucleating agent and water, preferably $D_2O$. The latex material can be acrylic, natural, nitrile, polychloroprene, paraffin, polyethylene, waxes, such as carnauba, styrene-butadiene, or vinyl pyridine based or mixtures thereof. Other potentially suitable latexes include styrene polymers, styrene/butadiene copolymers, styrene/acrylic acid copolymers, vinyltoluene/tertiarybutyl styrene copolymers, vinylidene chloride/vinyl chloride copolymers or mixtures thereof. The latex material preferably has a particle size of about 0.05 microns and is present from less than about 5 to about 30 weight percent, preferably about 15 weight percent.

In some embodiments, a two-phase emulsion, such as an oil-in-water, a water-in-oil emulsion, or a similar type of emulsion employing a non-oil hydrophobic liquid. The emulsion has a composition such that, when a temperature condition is met, the two phases mix to form a combined phase. If the combined phase is formed, an apparent color change occurs in one or both of the phases, or in the combined phase. The color change is typically irreversible.

In some embodiments, a three-phase emulsion can be used as an indicator dispersion. Such an indicator dispersion includes a base phase, a barrier phase dispersed in the base phase, and an active phase dispersed in the barrier phase. Typically, the active phase is miscible with the base phase, the barrier phase is substantially insoluble in the base phase, and the active phase is substantially insoluble in the barrier phase. Thus, for example, an indicator dispersion could be an water-in-oil-in-water (w/o/w) emulsion, an oil-in-water-in-oil (o/w/o) emulsion, a water-in-wax-in-water dispersion, etc. The emulsion has a composition such that, when a temperature condition is met, the active phase and the base phase mix to form a combined phase. If the combined phase is formed, an apparent color change occurs in the indicator dispersion, such as in the combined phase, or in the dispersion as a whole. The color change is typically irreversible.

For an indicator dispersion having a color change affected by light scattering, an active phase may have any droplet size that results in light scattering by the active phase and/or the barrier phase so that light scattering at least partially masks or alters the color of the colorant. Scattering may increase as the size of dispersed particles decreases.

Some examples of useful oils or hydrophobic liquids include hydrocarbons such as heptane, octane, nonane, decane, undecane, dodecane, tridecane, hexadecane and the like, either linear or branched; aromatics such as toluene, xylene, etc., mineral oil, terphenyl oils, etc.; esters, including vegetable oils, such as soybean oil, cottonseed oil, linseed oil, rapeseed oil, castor oil, sunflower oil, olive oil, kernel oil, peanut oil, corn oil, canola oil, coconut oil, hazelnut oil, avocado oil, almond oil, arachis oil, safflower oil, maize oil, soybean oil, caraway oil, rosemary oil, peppermint oil, eucalyptus oil, sesame oil, coriander oil, lavender oil, citronella oil, juniper oil, lemon oil, orange oil, clary sage oil, nutmeg oil, tea tree oil, etc., liquid fatty acid esters, such as liquid fatty acid esters of lauric acid, palmitic acid, stearic acid, etc.; silicon oils, such as siloxanes, polysiloxanes, cyclopolysiloxanes, dimethicone, etc.; heteroatom functionalized hydrocarbons, including haloaromatic compounds such as halogenated aromatic compounds, phenols, alkoxyaromatics, perflouroalkanes, etc. A mixture of two or more oils can also be used. One suitable terphenyl oil is available under the product code MCS 2811 from Solutia, St. Louis Mo.

To help maintain the stability of the indicator dispersion, an indicator dispersion may include a dispersion stabilizer. Some examples of suitable dispersion stabilizers include surfactants, such as anionic surfactants, cationic surfactants, zwitterionic surfactants, non-ionic surfactants or combinations thereof. In addition to those described above, in some embodiments, surfactants can include fatty acid salts, linear alkyl benzene sulfonates, dialkyl phosphates, linear alcohol sulfates, alkylphenol ethoxylates, sulfonated alkylphenol ethoxylates, fatty acid ester ethoxylates, ethylene oxide propylene oxide block copolymers, fatty acid sulfonates, betaines, quaternary ammonium salts. In some embodiments, Span 80 (a non-ionic surfactant within HLB number of 4.3, also known as Arlacel 80 [1,4-anhydro-6-O-[(9Z)-9-octadecenoyl]-D-glucitol]) may be useful to stabilize the aqueous active phase in the hydrophobic phase. In some embodiments, Tween 80 (a non-ionic surfactant within our HLB number of 15, also known as polysorbate 80 [3,6-anhydro-2,4,5-tris-O-(2-hydroxyethyl)-1-O-{2-[(9Z)-9-octadecenoyloxy]ethyl]hexitol]) may be useful to stabilize the hydrophobic phase in the aqueous base phase. In some embodiments, the dispersion stabilizer may be sodium stearate, sodium dodecyl sulfate, ammonium lauryl sulfate, sodium laurel phosphate, betaine, lauryl amido propyl dimethyl betaine, dodecyl trimethyl ammonium chloride, benzalkonium chloride, sorbitan monolaurate, and oleyl alcohol.

In other embodiments, so called Pickering emulsifiers may be used either exclusively or in addition to those already delineated. These are solid particulates with appropriately modified surface chemistry. For example hydrophobically surface modified silica nanoparticles, such as Aerosil R972 (Degussa Corporation) and the like may be used to make an initial water-in-oil emulsion that is then converted into the w/o/w emulsion in a second step with a different surface modified particle. An example of such a particle being fumed silica whose surface has been modified by adsorption or chemisorption to give the right balance of hydrophilicity and hydrophobicity. Many different materials may be adsorbed onto the surface of appropriate particles including surfactants. Useful Pickering emulsifiers are not limited to silica particles. In fact, many different particulates, of any 3 dimensional shapes, such as spherical, platelet, irregular etc., may be used including, but not limited to colloidal alumina, colloidal yttria, colloidal zirconia, etc.

Other stabilizers may include water-soluble or water absorbing polymers such as poly(vinylpyrrolidone); polysaccharide derivatives, such as cellulose derivatives, including carboxymethylcellulose, hydroxypropylmethylcellulose, etc., hyaluronic acid derivatives, etc.; water-soluble acrylics, such as polyacrylic acid, polymethacrylic acid, etc.; polyethylene oxides; starches; guar; alginates; chitosan; etc. Any useful amount of dispersion stabilizer may be used, such as about 0.1% to about 10% or about 0.5% to about 5% by weight.

It can be helpful if a dispersed phase in a two-phase emulsion has an average droplet size near the wavelength range of visible light, such as about 10 nm to about 2000 nm, about 100 nm to about 1200 nm, about 350 nm to about 900 nm, or about 390 nm to about 700 nm.

For three-phase emulsions, it can be helpful if the aqueous active phase has an average droplet size near the wavelength range of visible light, such as about 10 nm to about 2000 nm, about 100 nm to about 1200 nm, about 350 nm to about 900 nm, or about 390 nm to about 700 nm.

For some three-phase emulsions, the barrier phase has an average droplet size near the wavelength range of visible light, such as about 10 nm to about 2000 nm, about 100 nm to about 1200 nm, about 350 nm to about 900 nm, or about 390 nm to about 700 nm.

It can be advantageous to make a conditional change indicator that is unaffected by the condition until it is activated by some means. For example, an activatable temperature exposure indicator may be made with an incomplete indicating composition that is unaffected by temperature, in one container of a two-container construction, with the component in the other container that will make the mixture temperature sensitive. The indicator is activated by allowing the contents of the two containers to mix. FIG. 14 illustrates a dual container activatable condition change indicator where the two containers are separated by an area where the top and bottom layers are bonded more weakly than around the perimeter of the indicator.

Figure 14A:
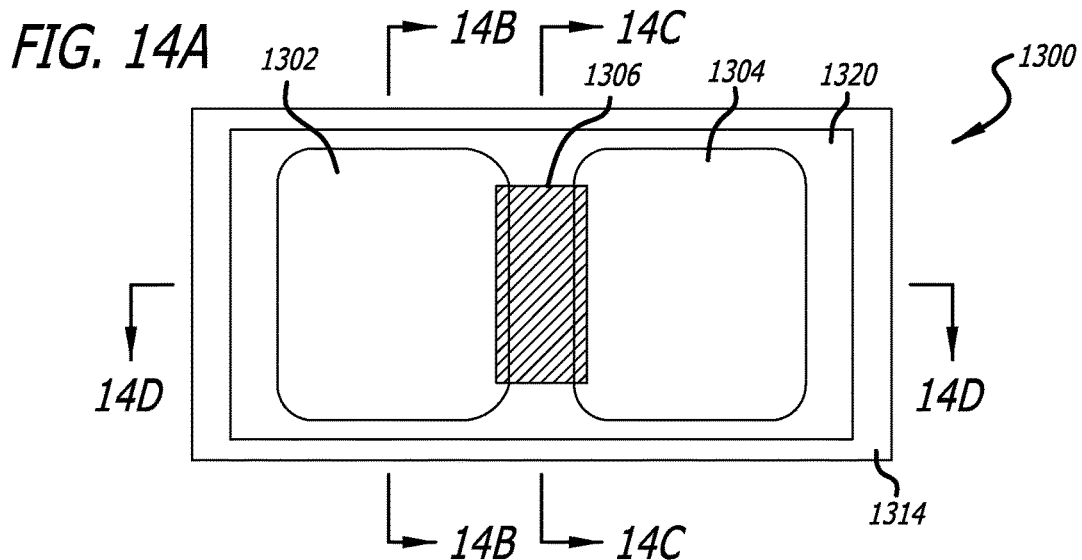
FIGS. 14A-D illustrate an example activatable condition change label.
Figure 14B:
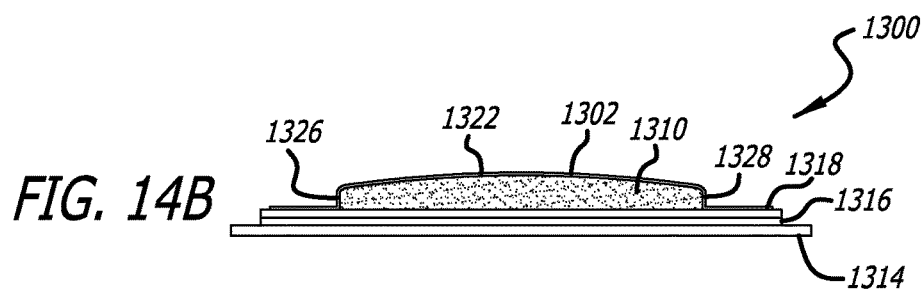
Figure 14C:
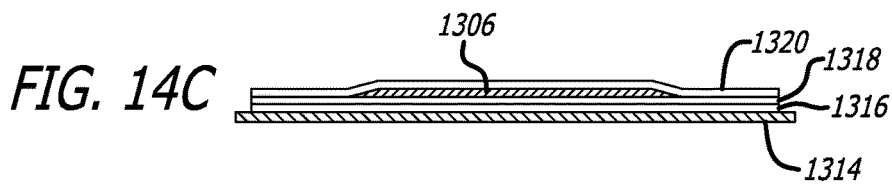
Figure 14D:
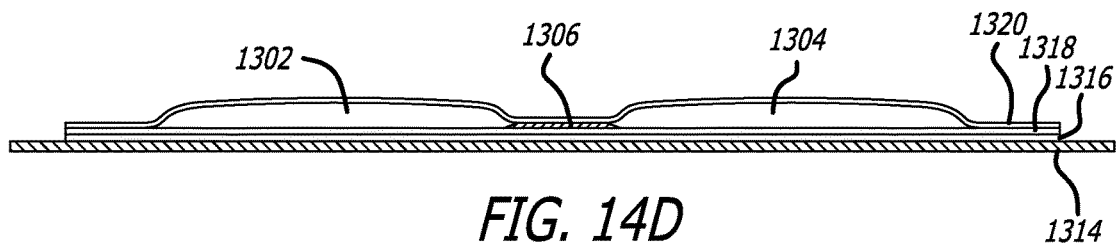

FIGS. 14A to 14D show the two blisters separated by a zone of low adhesion between top and bottom substrates. In FIG. 14A, label 1300 includes a first blister 1302 separated from a second blister 1304 by a weak adhesion area 1306. FIG. 14B shows that first blister 1302 and second blister 1304 are similar to blister 502 shown in FIG. 5A. First blister 1302 and second blister 1304 each house a respective indicator substance 1310, 1312. Before use, label 1300 is attached to a liner 1314 with an adhesive 1316 applied to bottom layer 1318. Here, blister 1302 has a lenticular shape 1322 toward its center. As stress is applied to label 1300, for example by placing the label 1300 on a cylindrical product housing 1324, first edge 1326 and second edge 1328 stretch in the z-spring direction thereby creating first tensioned edge and second tensioned edge. Weak adhesion area 1306 is located between top layer 1320 and bottom layer 1318. When the weak adhesion area 1306 is broken, indicator substance 1310 from first blister 1302 is free to mix with indicator substance 1312 from second blister 1304. That is, pressure on one of at least one of first blister 1302 and second blister 1304 can rupture the weak bond and permit the two fluids to mix. Such pressure may be produced for a label-like condition change indicator during the label application process.

The structure proposed for the activatable condition change indicator may be used to contain two reactive materials which it desirable to mix to initiate a reaction. On mixing the two materials shall begin to react and provide a useful mixture. For example one material may be a monomer mixture and the other a polymerisation catalyst. On mixing polymerization may begin and the mixture viscosity will increase. Such materials are well known as fillers for cracks, holes and other repairs.

EXAMPLES

Comparative Example 1

This indicator is described earlier and illustrated in FIG. 12B. An attempt to wrap an indicator on a 17 mm vial was unsuccessful—the rigid container prevented adjacent areas from contacting the vial, and the combination was too big to fit into a standard vial package. The construction without the blister, which is about 150 μm thick, has a resistance to bending (17 mm at 100 min) of 7.8 g/cm. Flagging propensity was assessed by removing the liner to expose the pressure sensitive adhesive, and then applying the construction firmly around a 12 mm freshly washed soda glass tube. It flagged in less than an hour. The construction appears unsuitable for direct attachment to a small vial.

Comparative Example 2

A freeze exposure indicator was formed on a blister machine. The transparent forming substrate was product VA 1090 from TekniPlex (a division of TekniFilms Somerville, N.J.). VA 1090 is a laminate of 250 μm PVC and 22 μm PCTFE. It has standard WVTR of about 0.23 g/m²/day. The blister had a volume of about 40 μl and contained an aqueous indicator suspension. The second substrate was TekniLid™ 1252, which is described by the manufacturer (TekniFilms, Somerville, N.J.) as an over-lacquer/aluminum/heat-seal-lacquer base on PVC and PVDC. TekniLid 1252 is essentially impervious to water vapor. The indicator was too stiff to be formed into a 17 mm semicircle. The construction was not suitable for use as an on-vial indicator.

The following are the laminates formed where the top film and the bottom substrate are bonded. The laminate must have the flexibility to wrap and not flag.

Example 1

A construction representing the combined top film and bottom substrate of a condition change indicator was prepared by bonding 25 μm clear biaxially oriented polyester film to clear 15 μm Aclar® transparent formable film with a pressure sensitive transfer adhesive. Aclar® is polychlorotrifluoroethylene (PCTFE), a product of Honeywell, Morristown, N.J. The combination had a resistance to bending of 0.48 g/cm at 17 mm, and expected WVTR of 0.33 g/m²/day. Flagging propensity was assessed by first applying FLEXmount TT200 L344 transfer adhesive, a product of FLEXcon, Spencer, Mass., with a roller, cutting a rectangle about 15 mm wide and 30 mm in the indented direction of wrap, and applying this firmly to a freshly cleaned 13 mm diameter soda glass tube. The tube was placed upright in a rack kept at room temperature and the material inspected for flagging periodically. This example had not flagged when inspected after 3 years. It appears suitable for use as an on-vial condition change indicator.

Example 2

A further construction was prepared from 25 μm PET and 22 μm Aclar® in the same manner as Example 1. It had a resistance to bending of 0.55 g/cm at 17 mm, and had not flagged after 3 years. It appears suitable for use as an on-vial condition change indicator.

Example 3

A further construction was prepared from 25 μm PET and 50 μm Aclar® in the same manner as Example 1. It had a resistance to bending of 1 g/cm at 17 mm, and had not flagged after 3 years. It appears suitable for use as an on-vial condition change indicator.

Example 4

A construction representing the combined top film and bottom substrate of a condition change indicator was prepared by bonding lidding stock 3078231 (a laminate of 20 μm hard tempered aluminum foil with 12 μm PET available from Constantia Hueck Foils, LLC Blythewood, S.C.) 50 μm Aclar® the heat seal adhesive of the lidding stock. The combination had a resistance to bending at 30 seconds of 3.0 g/cm and demonstrated flagging in less than 4 days. It does not appear suitable for use as a condition change indicator for 17 mm diameter or smaller vials.

Example 5

A construction representing the combined top film and bottom substrate of a condition change indicator was prepared by heat bonding TekniSeal product HS 165, a laminate of 25 μm tempered aluminum foil with 12 μm PET available from TriSeal, Flemington, Pa., to 50 μm Aclar® with the heat seal adhesive on the PET. The combination had a resistance to bending at 30 seconds of 2.9 g/cm. It was resistant to flagging for more than 3 years. It appears suitable for use as an on-vial condition change indicator.

Example 6

A coating of a 25% dilution of Michem® MP5931 ethylene acrylic acid suspension (available from Michelman, Cincinnati, Ohio) was applied with a No 4 Meyer rod to the barrier side of a sheet of Camclear® 48G PET. Camclear® 48G is 12 μm PET with an aluminum oxide barrier coat and a protective polymer coating available from Celplast Metallized Products, Toronto ONT.) The adhesive was dried at about 60° C. The dry coat weight was less than 1 g/m². The sample was heat laminated to the oxide side of another sheet of Camclear® 48G to form a construction representing the combined top and bottom substrates of a condition change indicator. The laminate was robust. It had an average resistance to bending after 30 seconds at 17 mm radius of 0.1 g/cm. This indicates that ceramic barrier coated film can be bonded with very thin heat seals to form highly flexible laminates potentially useful in the construction of on-vial condition change indicators.

Example 7

Sample 7 was repeated except that the adhesive coated film was heat laminated to the PET side of product A-10-NPS, a laminate of 8 μm aluminum foil with 12 μm PET available from Lamart, Clifton, N.J. The laminate had a resistance after 30 seconds to bending through 17 mm diameter of 0.7 g/cm, indicating suitability for use in an on-vial indicator.

Example 8

A condition change indicator is formed in the following manner. A blister about 100 μm deep and about 5 mm in diameter is formed in a sheet of 12 μm thick polyester film coated with a transparent high moisture barrier material. The blister is filled with about 2 μl of indicator fluid then sealed to a substrate of 24 μm white polyester film laminated to 12 μm aluminum foil. This structure in turn is laminated to a 10 μm pressure sensitive adhesive carried on a 24 μm release coated polyester liner. A 10 mm diameter circle is die cut in the indicator laminate around the blister, and the outer part removed to leave a 10 mm diameter indicator on a liner. The greatest thickness of this construction is about 0.17 mm.

| Example | Top substrate | Bottom Substrate | Resistance to bending 17 mm, (g/cm) |
|---|---|---|---|
| 1 | 15 μm Aclar ® | 25 μm PET | 0.48 |
| 2 | 22 μm Aclar ® | 25 μm PET | 0.55 |
| 3 | 50 μm Aclar ® | 25 μm PET | 1.0 |
| 4 | 50 μm Aclar ® | 12 μm PET laminated to 20 μm aluminum foil | 3.0 |
| 5 | 50 μm Aclar ® | 12 μm PET laminated to 20 μm aluminum foil | 2.9 |
| 6 | 12 μm PET with oxide coating | 12 μm PET with oxide coating | 0.1 |
| 7 | 12 μm PET with oxide coating | 12 μm PET8 μm laminated to 8 μm aluminum foil | 0.7 |

A roll of flexible material 0.17 mm thick wound on a 3 inch diameter core to a diameter of 10 inches holds 850 feet. 10 mm diameter indicators can be spaced 2 mm apart. The number of indicators made according to Example 8 on a 10 inch diameter roll may therefore exceed 20,000.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

I claim:

1. A flexible label including:
    a first layer including a blister laminated to a first side of a bottom layer thereby creating a container;
    a substance located in the container; and
    an adhesive disposed on at least a portion of a second side of the bottom layer wherein the label has a stiffness less than about 0.06 mN·m;
    wherein the blister is shaped to minimize the visual impact on the substance in the container when the label is applied to a curved surface.

2. The label of claim 1, wherein the substance is an indicator substance.

3. The label of claim 2, wherein the stiffness is between about 0.001 mN·m and about 0.06 mN·m.

4. The label of claim 2, wherein the first layer is substantially transparent.

5. The label of claim 2, wherein the bottom layer is opaque.

6. The label of claim 2, wherein the indicator substance or condition change indicator substance is a solid, a liquid, a gel, a semi-solid, a colloid, a mesh, or a combination thereof that is configured to change state, color, transparency, or a combination thereof upon introduction to the predetermined condition.

7. The label of claim 6, wherein the predetermined condition is freezing, boiling, exposure to light, exposure to humidity, exposure to excess pressure, subject to contamination, or a combination thereof.

8. The label of claim 7, wherein the predetermined condition is freezing.

9. The label of claim 2, wherein the label is sufficiently flexible to wrap around a product container without flagging.

10. The label of claim 9, wherein the product container is a cylindrical product container.

11. The label of claim 9, wherein the cylindrical product container has a diameter of 16 millimeters or more, or of 12 millimeters or more, or of 8 millimeters or more.

12. The label of claim 2, wherein the first layer comprises polypropylene, polyester, polychlorotrifluoroethylene, transparent barrier coatings or combinations of polypropylene, polyester, polychlorotrifluoroethylene, and transparent barrier coatings.

13. The label of claim 2, wherein the second layer comprises polypropylene, polyester, polychlorotrifluoroethylene, barrier coatings, vacuum deposited aluminum, tempered aluminum foil, annealed aluminum foil or combinations of polypropylene, polyester, polychlorotrifluoroethylene, barrier coatings, vacuum deposited aluminum, tempered aluminum foil or annealed aluminum foil.

14. The label of claim 2, wherein the label is sufficiently rigid to detach from a liner.

15. The label of claim 2, having a liner attached to the adhesive.

16. The label of claim 15, wherein the total thickness of the first layer, the bottom layer, the adhesive and the liner is less than 3 mm.

17. A method of forming the label of claim 2, comprising:
laminating the first layer to the second layer thereby encasing the indicator substance.

18. The method of claim 17, further comprising applying the adhesive to the second side of the second layer.

19. The label of claim 1, which is a condition change label.

20. A label, which is an activatable condition change label, including:
- a first layer including a first and a second blister laminated to a first side of a bottom layer thereby creating two containers;
- an inactive condition change indicator substance located in the first container;
- a liquid activator substance for the inactive condition change located in the second container;
- an area of weak adhesion between the top film and the bottom layer in the area between the two containers such that pressure on the second container can force the activator liquid into the first container thereby activating the condition change indicator substance so as to allow it to undergo a change in visual appearance upon introduction to a predetermined peak condition;
- an adhesive disposed on at least a portion of a second side of the bottom layer, wherein the condition change label has a stiffness less than about 0.06 mN·m;
- wherein the first and/or second blister is shaped to minimize the visual impact on the condition change indicator when the label is applied to a curved surface.

* * * * *